United States Patent [19]

Pyle et al.

[11] Patent Number: 5,872,241
[45] Date of Patent: Feb. 16, 1999

[54] MULTIPLE COMPONENT RNA CATALYSTS AND USES THEREOF

[75] Inventors: Anna M. Pyle; William J. Michels, both of New York, N.Y.

[73] Assignee: The Trustees of Columbia University in the City of New York, New York, N.Y.

[21] Appl. No.: 378,235

[22] Filed: Jan. 25, 1995

[51] Int. Cl.[6] .......................... C07H 21/00; C07H 21/02; C12P 19/34; C12Q 1/68
[52] U.S. Cl. .......................... 536/24.5; 435/6; 435/91.31; 435/375; 514/44
[58] Field of Search .............................. 435/172.3, 91.31, 435/199, 6, 375; 514/44; 536/23.1, 23.2, 24.3, 24.31, 24.32, 24.5

[56] References Cited

U.S. PATENT DOCUMENTS

| | | | |
|---|---|---|---|
| 4,987,071 | 1/1991 | Cech et al. | 435/91.31 |
| 5,168,053 | 12/1992 | Altman et al. | 514/44 |
| 5,254,678 | 10/1993 | Haseloff et al. | 536/23.2 |
| 5,298,612 | 3/1994 | Jennings et al. | 536/23.2 |
| 5,585,479 | 12/1996 | Hoke et al. | 536/24.5 |

FOREIGN PATENT DOCUMENTS

| | | |
|---|---|---|
| 360257 | 3/1990 | European Pat. Off. . |

OTHER PUBLICATIONS

Gewirtz et al. "Facilitating oligonucleotide delivery: Helping antisnese deliver on its promise" Proc. Natl. Acad. Sci. USA 93: 3161–3163, Apr. 1996.
Bachl, J. and C. Schmelzer, (1990) "Effect of Deletions at Structrual Domains of Group II Intron bI1 on Self–splicing in Vitro" J.Mol. Biol. 212: 113–125.
Cech, T.R. (1986) "The Generality of Self–Splicing RNA: Relationship to Nuclear mRNA splicing" Cell 44: 207–210.
Cech, T.R. et al. (1992) "RNA Catalysis By a Group I Ribozyme" J. of Biol. Chem. 267(25): 17479–17482.
Jacquier, A. and N. Jacquesson–Breleux (1991) "Splice Site Selection and Role of the Lariat in a Group II Intron" J. Mol. Biol. 219: 415–428.
Jaquier A. and F. Michel (1987) "Multiple Exon–Binding Sites in Class II Self–Splicing Introns" Cell 50: 17–29.
Jacquier, A. and M. Robash (1986) "Efficient Trans–Splicing of a Yeast Mitochondrial RNA Group II Intron Implicates a Strong 5' Exon–Intron Interaction" Science 234: 1099–1104.

Jarrell, K.A. et al. (1988) "Group II Intron Domain 5 Facilitates a trans–Splicing Reaction" Molecular and Cellular Biology 8: 2361–2366.
Michel, F. et al. (1989) "Comparative and Functional Anatomy Of Group II Catalytic Introns—A Review" Gene 82:5–30.
Michels, William J. and A.M. Pyle (1994) "A New Group II Intron Ribozyme: Kinetic Framework and Stereospecificity" Abstract and Poster for RNA Processing Meeting of the RNA Society, University of Wisconsin–Madison, May 24–29, 1994.
Peebles, C.L., et al. (1986) "A Self–Splicing RNA Excises an Intron Lariat" Cell 44: 213–223.
Pyle, A.M. (1993), "Ribozymes: A Distinct Class of Metalloenzymes" Science 261: 709–714.
Pyle, A.M. and J.B. Green (1994) "Building A Kinetic Framework for Group II Intron Ribozyme Activity: Quantitation of Interdomain Binding and Reaction Rate" Am. Chem. Soc. 33:2716–2725.
Pyle, A.M. et al., (1990) "Direct measurement of oligonecleotide substrate binding to wild–type and mutant ribozymes from Tetrahymena" Proc. Natl. Acad. Sci. USA 87: 8187–8191.
Sharp, Phillip A. (1988) "RNA Splicing and Genes" JAMA 260: 3035–3041.
Wise, Jo Ann (1993) "Guides to the Heart of the Spliceosome" Science 262: 1978–1979.

*Primary Examiner*—George C. Elliott
*Assistant Examiner*—Thomas G. Larson
*Attorney, Agent, or Firm*—John P. White; Cooper & Dunham LLP

[57] ABSTRACT

This invention is directed to a composition for catalyzed oligonucleotide cleavage comprising a synthetic non-naturally occurring oligonucleotide compound. The compound comprises nucleotides whose sequence defines a conserved group II intron catalytic region and nucleotides whose sequence is capable of hybridizing with a predetermined oligonucleotide target sequence to be cleaved, such target sequence not being present within the compound. The composition also includes an appropriate oligonucleotide co-factor. Preferably, the conserved group II intron catalytic region is a group II intron domain I catalytic region. In one embodiment the conserved group II intron domain I catalytic region may further comprise a conserved portion of a group II intron domain II, a group II intron domain III, a group II intron domain IV, a group II intron domain V, or a group II intron domain VI. The invention is also directed to methods of treatment and methods of use of such compounds.

22 Claims, 17 Drawing Sheets

Group I
Self-Splicing

Group II
Self-Splicing

Nuclear mRNA
Spliceosomal

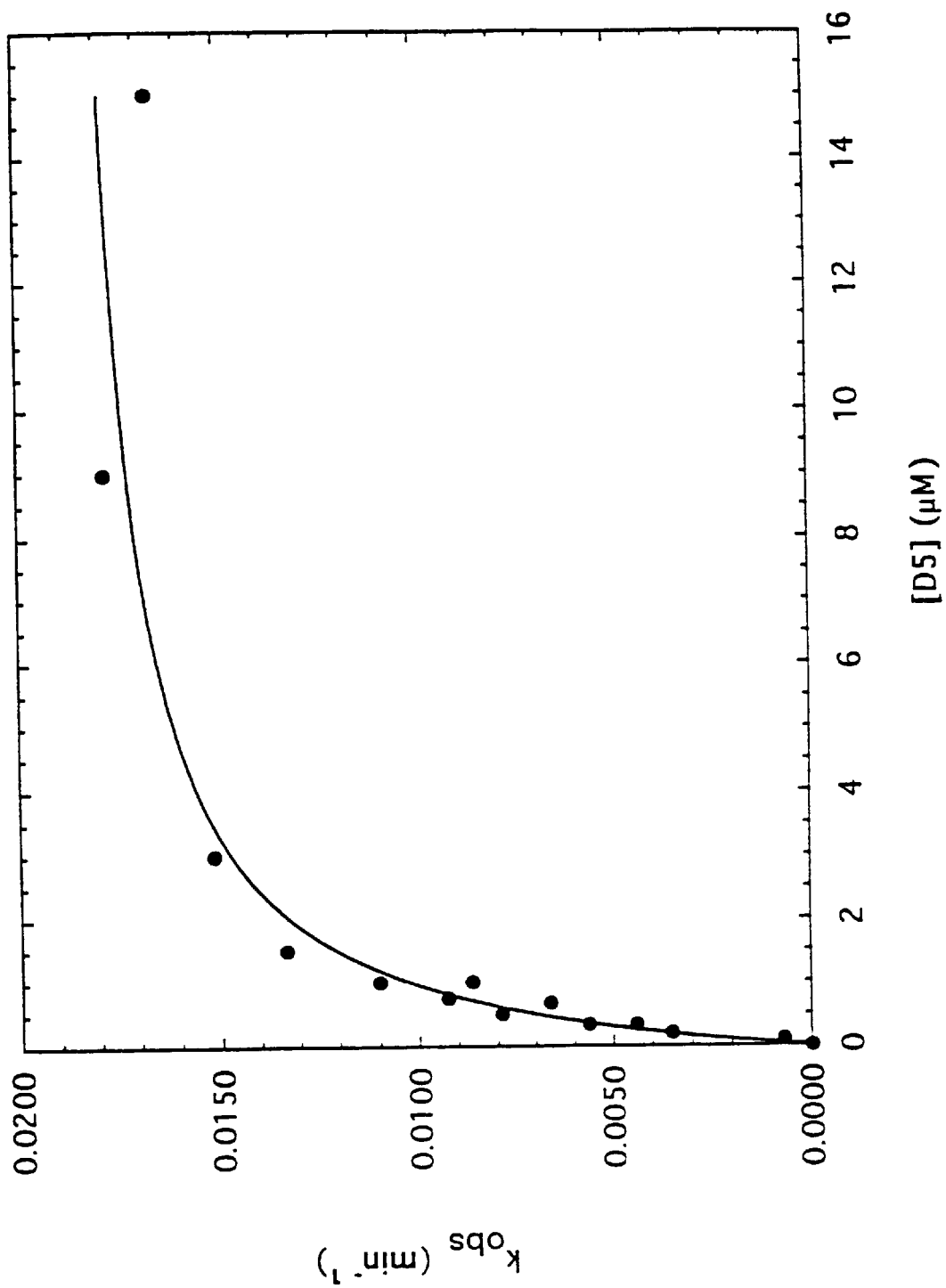

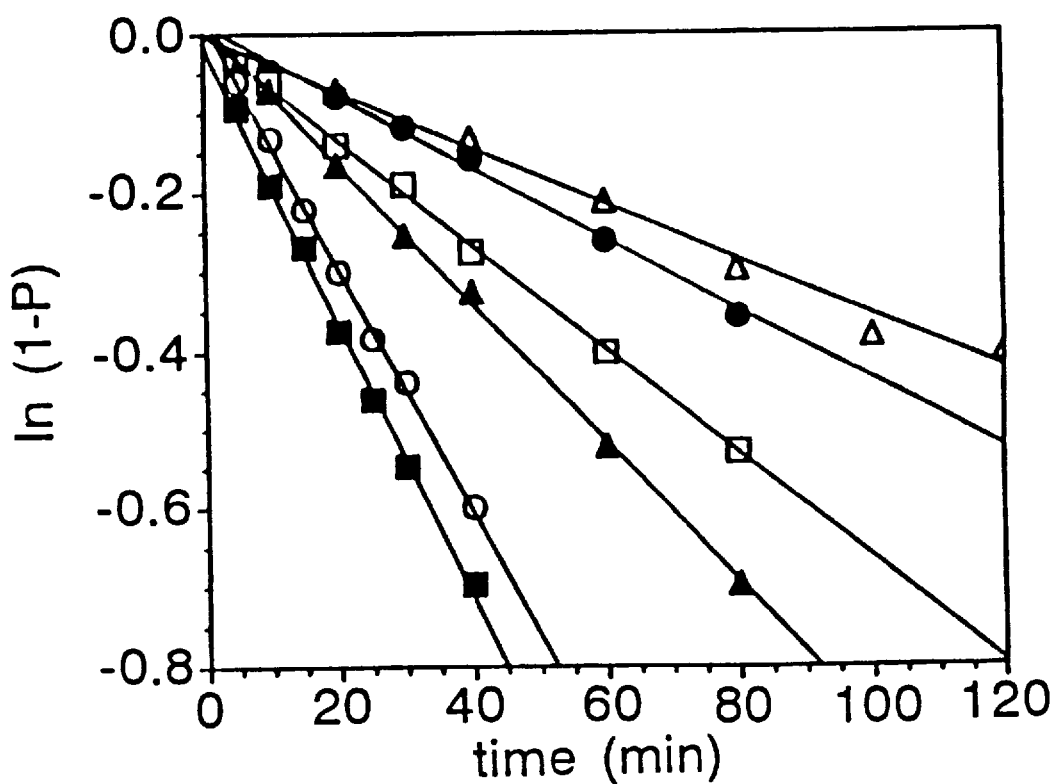

FIG. 9A $$5'\text{-}\overset{-19}{\text{GGAGUGUGGACAUUUUC}}\overset{-1\ +1}{/}\overset{+8}{\text{GAGCGGUU}}\text{-}3'$$

| 1 | 2 | 3 | 4 | 5 | 6 | |
|---|---|---|---|---|---|---|
| − | − | + | + | − | − | D1 |
| − | − | − | − | + | + | D5 |

*pCpsGpsG

*pCpsG

*pC

MULTIPLE COMPONENT RNA CATALYSTS AND USES THEREOF

BACKGROUND OF THE INVENTION

The invention disclosed herein was made with Government support under NIH Grant No. GM 50313-01 from the Department of Health and Human Services. Accordingly, the U.S. Government has certain rights in this invention.

Throughout this application various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

In 1977 a discovery was made which radically modified our understanding of gene expression. Two laboratories observed that the protein coding sequences of an adenovirus gene are interrupted by regions of encoding DNA (Berget, 1977; Chow, 1977). The sequences of these interrupting regions, or "introns", are transcribed into precursor mRNA, and excised from the parent RNA in a process called RNA splicing. The coding ends of mRNA are then joined together, resulting in "processed" mRNA which is ready to code for protein. Comparison of genomic and RNA sequences revealed that introns are actually quite common in eukaryotic genes. Many genes contain multiple introns, and by splicing them out and religating the coding regions together in different combinations, a single gene can produce multiple protein products. This imparts an additional degree of control and versatility to the expression of eukaryotic genes.

It was subsequently learned that a host of proteins and five nuclear RNAs (snRNAs) assemble as a complex upon nascent transcripts of pre-mRNA. This protein/RNA assembly was found to be responsible for catalyzing the splicing reaction and was appropriately dubbed the "spliceosome" (Brody, 1985). Analysis of reaction products showed that the spliceosome facilitates nucleophilic attack of an adenosine within the intron upon a phosphodiester bond at the 5'-intron/exon boundary to generate a branched intermediate (FIGS. 1A–1C). The liberated 5'-exon then attacks at the 3'-exon-intron boundary, resulting in ligation of the two exons (thus generating coding mRNA) and excision of a lariat-shaped intron (Guthrie, 1991) (FIGS. 1A–1C).

Not long after the discovery of RNA splicing, workers in the laboratory of Thomas Cech observed that precursor ribosomal RNA from Tetrahymena thermophila was capable of undergoing an in-vitro splicing reaction in the absence of protein enzymes (Kruger, 1982). Although it was assumed that a complement of endonucleases and ligases were involved in the two transesterifications required for splicing, the Cech lab showed that a structure within the folded intron itself catalyzed the splicing reaction in the presence of Mg2+ and a guanosine cofactor. This was the first example of a catalytic RNA, or ribozyme, in which RNA itself was capable of behaving like an enzyme.

It appeared that "self-splicing" by Tetrahymena intron (phylogenetically classified as a group 1 intron) was fundamentally different from pre-mRNA splicing because of structural differences in their reaction products (Cech, 1986).

Several years later, members of the group II family of introns were observed to undergo a self-splicing reaction in-vitro (Peebles, 1986; van der Veen, 1986). Group II introns are unrelated to the group I introns in sequence or secondary structure and, although group II introns undergo a self-splicing reaction, their reaction products are most similar to those of pre-mRNA splicing (FIGS. 1A–1C). Like pre-mRNA splicing, the first step of group II self-splicing involves attack of an internal adenosine residue rather than a bound guanosine, and after splicing is complete, group II introns are excised as lariats. Additionally, the sequences surrounding the splice sites near group II introns and pre-mRNAs are very similar. For these reasons, group II introns have often been referred to as the "missing link" between group I introns, which are believed to represent a sort of molecular fossil of primitive RNA processing, and the splicing of pre-mRNA which is a relatively modern development (Cech, 1968; Jacquier, 1990). It has been proposed that the subdomains of the group II intron are analogous to mRNA molecules within the spliceosome and, since characterization of the unimolecular group II ribozyme would be far easier than dissection structure and mechanism of the spliceosome, study of group II intron ribozymes provides an important basis for our understanding of RNA splicing in general. Additionally, a functional analogy between group II intron subdomains and snRNAs would support the theory that eukaryotic prem-RNA processing is catalzyed by RNA components of the spliceosome.

Instead of proteins and snRNAs, the active site of the group II intron is composed of a single strand of folded RNA. This RNA is divided into six domains (FIGS. 2A–2B), which may, like snRNAs and proteins, function separately in composing the active site and catalyzing the splicing reaction (Michel, 1989). It has therefore been of interest to define the functions of the individual domains. Techniques of molecular genetics have shown that Domains 2, 4 and most of 3 can be replaced by short hairpin loop regions without detectable effects on self-splicing (Bachl, 1990; Kwakman, 1989). Domain 1, which is the largest, recognizes the 5'-exon by base-pairing and participates in several other important stabilizing interactions (Jacquier, 1991). The most conserved region of the group II intron and the one with the greatest effects on splicing is Domain 5. This short hairpin region of RNA (only 34 nucleotides in the ai5g intron) appears to direct the folding or activity of the group II intron in a very fundamental way (Jarrell, 1988; Pyle, 1994).

In 1988, the laboratory of Philip Perlman found that a group II construct containing only Domains 1–3 was unable to undergo the first step of splicing. However, addition of the tiny Domain 5 in-trans rescued the splicing reaction (Jarrell, 1988). Direct proof of the strong D5 tertiary interaction was provided by kinetic and thermodynamic studies showing D5 bonds in trans with a KD of ≈300 nM. (Pyle, 1994). Given that Domain 5 is almost completely paired and there is no phylogenetic covariation between sequences in Domains 1 and 5 (Michel, 1989), it is highly unclear how it would associate with Domain 1 to generate the catalytically active structure.

With the finding that group II intron structures are formed during the trans-splicing of mitochondrial energetics genes from higher plants (Wissinger, 1992), it is now believed that group II splicing reactions are of general importance. They are central to the metabolism of plants, yeast and possible other eukaryotes. Some group II introns contain open reading frames which code for "maturases", or proteins which assist in the splicing and reverse-splicing of group II introns in-vivo (Perlman, 1989). Some of these maturases contain reverse ranscriptase and RNase H domains (Lambowitz, 1990). These findings have precipitated interest in the introns as mobile genetic elements, or "infectious" RNAs, readily able to integrate into new genomes (Lambowitz, 1989). Interestingly, open reading frames and base-pairing recognition domains for trans-splicing variants of the group II intron are usually found in Domains 2 or 4 of the group II structure, regions of high variability and low sequence conservation (Michel, 1989).

Although group II intron reactions are important in their own right, the greatest interest in group II introns stems from the hypothesis that they are related chemically and structurally to the spliceosomal apparatus responsible for eukaryotic pre-mRNA processing (Sharp, 1985). This theory implies that the group II intron may be used as a model for reactions which take place in the spliceosome, a reaction center which is extremely difficult to characterize because it contains hundreds of components and must be assembled in cell extracts. It also suggests that group II intron chemistry will describe "remnants" of RNA catalysis still present in higher biological systems and suggests that spliceosomal processing is RNA-catalyzed despite the presence of proteins. There is a great deal of chemical theory which now supports these ideas. Work by Moore, Sharp and coworkers on the stereochemistry at pre-mRNA splice sites has provided evidence for the involvement of two active sites in spliceosomal catalysis (Moore, 1993). This suggests that group II introns may also have two active sites; one for the first step and one for the second step of splicing. Group I introns are generally believed to have only one active site, and that is why the stereochemistry of nucleophilic attack in the first step is opposite to that of the second step [24, 25] (McSwiggen, 1989; Rajogopal, 1989). Spliceosomal processing and group I introns are most similar in the second step of splicing, where both prefer the pro-S isomer of phosphate. Spliceosomal processing and group II introns appear most similar in the first step which is initiated by adenosine 2'-OH attack. This implies that the first step in group II intron splicing is most likely to represent a new form of catalytic active site and one which we must characterize before we can understand the relationship to pre-mRNA processing. To this end, engineering multiple-turnover ribozymes from the group II intron will enable us to examine the chemical mechanism for reactions catalyzed by the active site(s) of the group II intron. This same approach was a prerequisite to characterization of the transition state, the active-site structure and the detailed mechanism descriptive of the group I intron (Cech, 1992).

It was originally believed that in-vitro group II self-splicing was inefficient before appropriate reaction conditions were defined in 1988 (Jarrell, 1988). Despite splicing reactions which are complete within minutes and the fact that splicing is a complicated multi-step process, the belief that group II introns have lumbering reactivity still persists. It is also commonly believed that the structure of the group II intron is metastable, with few molecules in a pool assuming an active conformation. Unfortunately, there is little quantitative data to substantiate either of these theories. Many generalized ideas about the nature of the group II intron come from observations of a single molecule, particularly the ai5g intron from yeast mitochondria. There have been no systematic comparisons of group II intron reactivity of stability, and virtually no quantitative analysis on the kinetic behavior of any single intron. We know nothing about the architecture of the folded structure. Clearly, before the group II intron can be discussed coherently as a model for pre-mRNA processing, we must characterize much of its fundamental behavior. As indicated above, the most rapid way to do this is to transform the unimolecular group II self-splicing reaction into multiple-turnover ribozyme that function under simple conditions. This will impart significant control over the reaction and facilitate careful mechanistic analysis of the intron.

Several research groups have been pursuing the use of catalytic RNA, also known as ribozymes, for uses in diagnostics, as restriction enzymes, see for example Cech et al. U.S. Pat. No. 4,987,071. Ribozymes which are highly specific in the recognition sequences offer potential in therapy for plants or mammals, see for example Haseloff et al. U.S. Pat. No. 5,254,678 for hammerhead ribozymes, Jennings et al. U.S. Pat. No. 5,298,612 for minizymes; Hampel et al. European Appn. No. 89 117 424.5, filed Sep. 20, 1989 for hairpin ribozymes; and Altman et al. U.S. Pat. No. 5,168,053, for prokaryotic RNAase P. However, this is the first report of the use of a modified group II intron composition to act in trans, i.e. as a catalyst, to cleave a nucleic acid target.

SUMMARY OF THE INVENTION

This invention is directed to a composition for catalyzed oligonucleotide cleavage comprising a synthetic non-naturally occurring oligonucleotide compound. The compound comprises nucleotides whose sequence defines a conserved group II intron catalytic region and nucleotides whose sequence is capable of hybridizing with a predetermined oligonucleotide target sequence to be cleaved, such target sequence not being present within the compound. The composition also includes an appropriate oligonucleotide co-factor. Preferably, the conserved group II intron catalytic region is a group II intron domain I catalytic region. In one embodiment the conserved group II intron domain I catalytic region may further comprise a conserved portion of a group II intron domain II, a group II intron domain III, a group II intron domain IV, a group II intron domain V, or a group II intron domain VI. The invention is also directed to methods of treatment and methods of use of such compounds.

BRIEF DESCRIPTION OF THE FIGURES

FIG. 2B—Seq. ID Nos. 7 and 8).

(FIG. 4A) Domain 1 (D1) combines with Domain 5 (D5) and substrate (S) to catalyze specific cleavage at a site analogous to the 5'-splice site. Shaded regions and dashes between D1 and S designate pairing interactions IBS1:EBS1 (closest to the cleavage site) and IBS2:EBS2. D1 RNA (425 nts) was transcribed from plasmid pT7D1 cut with Eco RI. This plasmid was constructed by PCR amplification of D1 from the full-length plasmid pJD20 (Jarrell, 1988). Primers specifically amplified a 425 nt intronic fragment including all of D1 beginning with the +1 nucleotide of the intron (G). The upstream primer included a T7 promoter sequence and a BamHI restriction site. The downstream primer contained an EcoR1 site. The PCR fragment was ligated into a pUC19 vector, expressed and sequenced. D5 was transcribed as previously described from plasmid pJDI5'-75 (kindly provided, together with pJD20 by Dr. Philip S. Perlman) (Pyle, 1994).

Transcribed substrates were made using T7 RNA polymerase using synthetic DNA oligonucleotide templates according to published procedures. All RNAs were purified as described (Pyle, 1994). (FIG. 4B) Ribozyme cleavage of substrate (S) 5'-$^{32}$P-GGA<u>GUGGUGGG</u>ACAUUUUC GAGCGGUU-3' (SEQ ID NO 1) to a 5'-end-labelled 19 nt. product (p) and an 8 nt. unlabelled product. The cleavage site is marked with a "" and IBS sequences are underlined. Lanes 1–8 correspond to a reaction of S (1 nM) in the presence of saturating D1 (100 nM) and saturating D5 (3 μM). The reaction was performed under standard reaction conditions: at 42° C. in 80 nM MOPS (pH 7.5), 1M KCl, and 100 nM MgCl$_2$. RNAs were mixed at 1.67× final conc. in 80 nM MOPS pH 7.5 and then heated to 95° C. for 1 min. to denature potentially mis-folded RNAs formed during storage. After cooling to 42° C., reaction was initiated by addition of 100 nM MgCl$_2$, 1M KCl and 80 nM MOPS (final concentrations). Aliquots of the reaction were removed at the time intervals specified in the figure, combined with denaturing dye on ice, loaded on a 20% denaturing polyacrylamide gel (PAGE) and quantitated as previously described.

FIGS. 5A–5D: Single-turnover kinetics of S cleavage by the three-part group II ribozyme. Rate constants and kinetic parameters (Table 1) were obtained by plotting pseudo-first order rates ($k_{obs}$), determined from the slope of inset plots against a reactant varied in concentration. It was determined that $k_{obs}$ values at saturation did not vary from 0.01 to 3 Nm [S], indicating that pseudo-first order kinetics apply (data not shown). Pseudo-first order semi-log plots of the cleavage timecourse were linear for >3 reaction half-times (see also FIG. 9B) Early time points (generally <50% completion) were used in the calculation of $k_{obs}$ (see also FIG. 9B). Individual values of $k_{obs}$ were determined over a 6 week time period with the same RNA stocks and varied by 18% (with 95% confidence and 5 trials). The 24-nucleotide substrate, CGUGGUGGGACAUUUUCGAGCGGU (SEQ ID NO 2), was made synthetically (Scaringe, 1990). The empirically determined endpoint for reaction of this substrate was 80% after >7 reaction half-times. This value was used in correction of all pseudo-first order plots used in this figure. FIGS. 5A and 5B Inset: Representative pseudo-first order plots for cleavage of S (0.05 nM) at saturating D5 (3 μM) and varying concentrations of D1 (0.5, 1.5, 3.25, 5, 10, 20, 100 nM shown). Hyperbolic plot: The $k_{obs}$ values determined from inset plots were graphed against [D1] to generate the apparent binding curve for D1. In both A and B hyperbolic plots, the $k_{max}$ value for the reaction is the horizontal asymptote of plots (~0.02 min$^{-1}$), and Km is the concentration of enzymatic subunit at which $k_{obs}$ is one-half $k_{max}$. FIGS. 5C and 5D Inset: Representative pseudo-first order plots for cleavage of S (0.1 nM) at saturating D1 (25 nM) and varying amounts of D5 (0.2, 0.33, 0.67, 1, 3, 9 μ.M shown). Hyperbolic plot: The $k_{obs}$ values determined from inset plots were graphed against [D5] to generate the apparent binding curve for D5 and the kinetic parameters shown in Table 1 (line 3).

In FIG. 8A: nuclease digestions of 5'-$^{32}$P end-labelled all-phosphate substrate described in the legend to FIG. 4. In FIG. 8B, the 5'-$^{32}$P end-labelled substrate was transcribed from the same DNA template, but α-thio (Sp) GTP (Amersham) was used as the sole source of GTP in the reaction. This substrate contains an Rp phosphorothioate residue at every G, including the cleavage site. Enzymatic digestions were carried out under standard conditions (Donis-Keller, 1977). For both A and B, Lane 1 is the full-length substrate. Lane 2 and 3 are digestions with hydroxide. Lane 4: Digestion with endonuclease U2 (BRL, cuts ApN). Lane 5: enzyme B. cereus (Pharmacia, cuts UpN or CpN), Lane 6: enzyme CL3 (BRL, cuts CpN), Lane 7: enzyme T2 (Pharmacia, cuts GpN), Lane 8: Ribozyme reaction product (19-mer RNAs), Lane 9: P1 nuclease (Boehringer Mannheim, no sequence specificity), Lane 10: Hydroxide ladder on substrate, Lane 11: P1 digestion of ribozyme reaction product (all-phosphate substrate only). Sequence specific nucleases cleave RNA to leave terminal 3' phosphate, while alkaline hydrolysis leaves predominantly 2'–3'-cyclic phosphates. P1 nuclease cleaves RNA to leave 3'-OH.

FIGS. 9A and 9B: (FIG. 9A). Quantitative determination of (Rp) phosphorothioate cleavage by the ribozyme. Phosphorothioate substrate was made by transcription of DNA template as in FIG. 8B, except labelling was accomplished by including a $^{32}$P CTP in the transcription reaction (Seq. ID NO. 9). Nuclease digestion of precursor substrates: RNA (3000 cpm) was incubated with 0.01 U/μl P1 nuclease in 25 mM acetate buffer pH 5.3, 10 mM DTT, and 0.05 μg/μl tRNA competitor for 30 min. at 37° C. Lane 1. Digestion of all-phosphate substrate with P1 nuclease. Lane 2: All-phosphate substrate digested with ribozyme, followed by P1. Lane 3: Digestion of thio-substrate with P1. Lane 4: Digestion of thio-substrate with ribozyme, followed by P1. Lanes 5 and 6: Digestion of thio-substrate with D1 and D5 alone, respectively, followed by P1. All ribozyme incubations were performed to completion under the conditions described in FIG. 6. following ribozyme digestion, RNAs were ethanol precipitated, resuspended and digested to completion with P1 nuclease (Lanes 1+3: 0.01 U/μl P1 nuclease in 25 mM acetate buffer pH 5.3, 10 mM DTT and 0.05 μg/μl tRNA competitor for 30 min. at 37° C. Lanes 2, 4, 5 and 6: as in Lanes 1 and 3 except tRNA was 0.025 μg/μl). Any radioactivity in the middle (*pCp$_s$G) band in lane 4 corresponds to counts from the small fraction of thio-substrate (~18%) that was uncleavable by the ribozyme (SEQ ID NO: 6). (FIG. 9B). Kinetics of transcribed ribozyme substrates: Cleavage of the (Rp)-phosphorothioate substrate (circles, described in FIGS. 8 and 9A) and the transcribed all-phosphate substrate (squares) follow pseudo-first order kinetics for more than three half-lives. Reaction conditions and saturating RNA concentrations were identical to FIG. 4, except [S] concentration was 0.1 nM. Values for $k_{obs}$ are 0.00094 and 0.032 min$^{-1}$, respectively (average of two determinations). For the thio-substrate, data is corrected for an empirically determined end-point (at 7 half-times) of 83%. The all-phosphate substrate data is corrected for an empirically determined endpoint of 96% (at >7 half-times).

DETAILED DESCRIPTION OF THE INVENTION

Figure 1A:
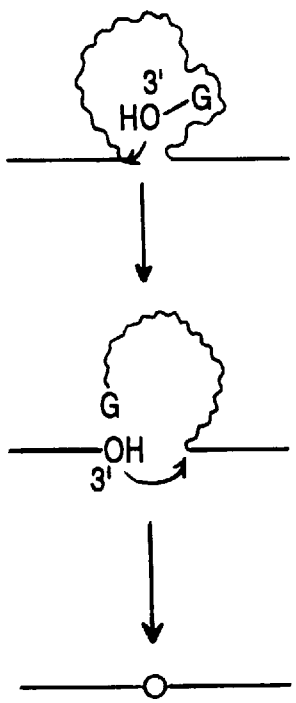
FIGS. 1A–1C: Shows a comparison of RNA processing by self-splicing introns and the spliceosomal apparatus.
Figure 1B:
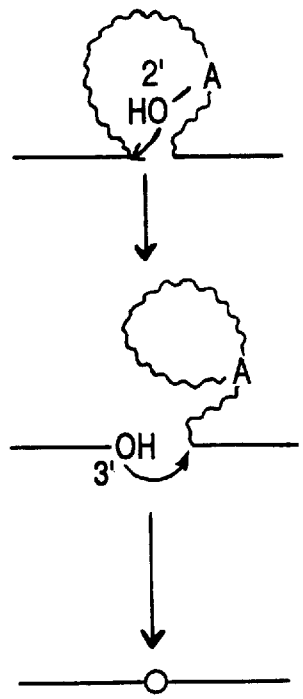
Figure 1C:
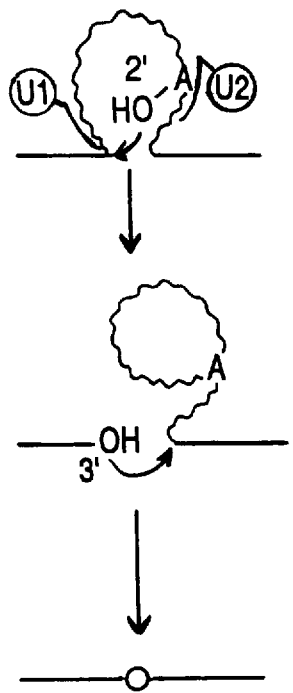
Figure 1C:
Figure 1C:
Figure 1C:
Figure 2A:
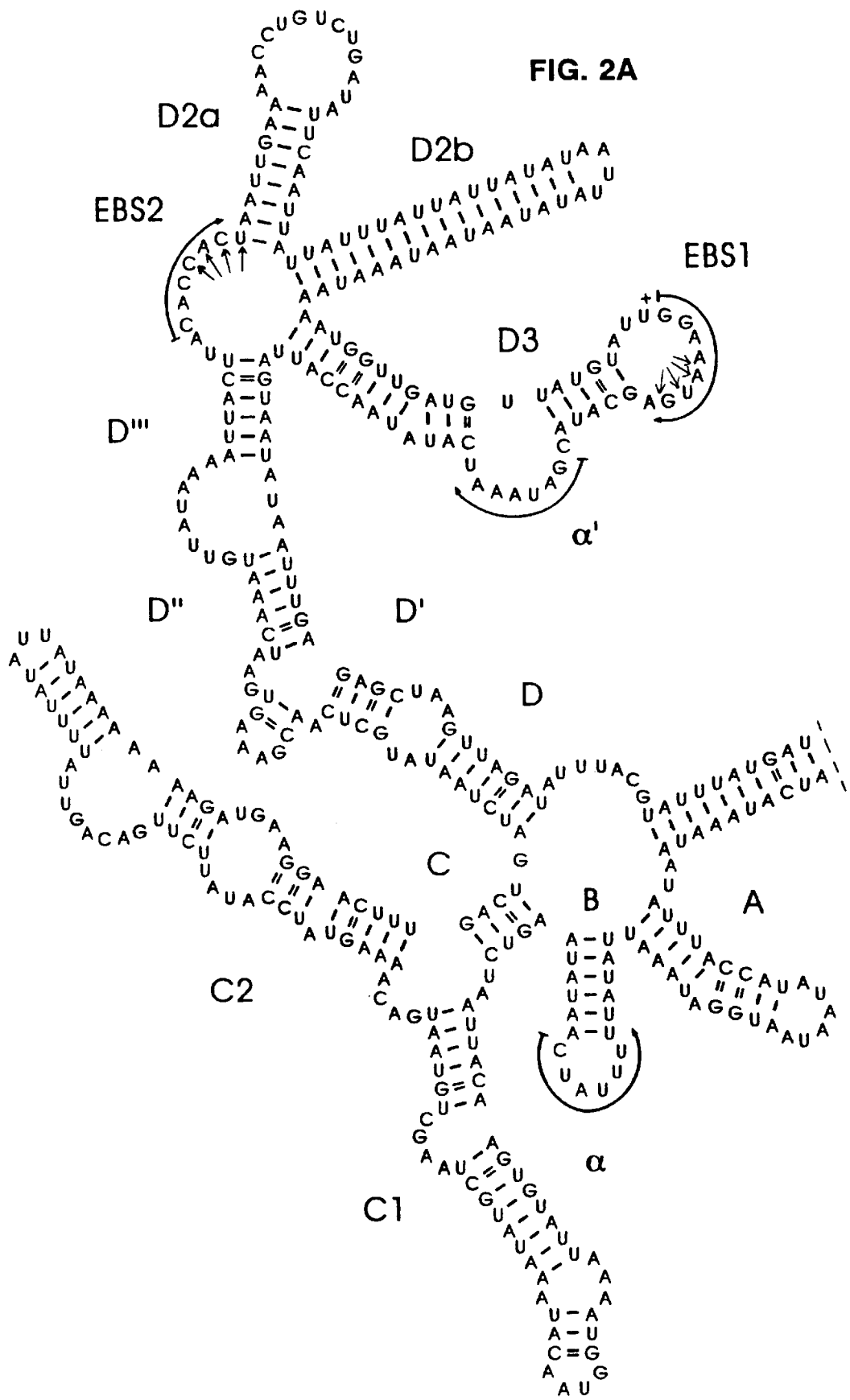
FIGS. 2A–2D: Shows the secondary structure of the two group II introns from yeast mitochondria (FIG. 2A—Seq. ID Nos. 4, 5 and 6.
Figure 2B:
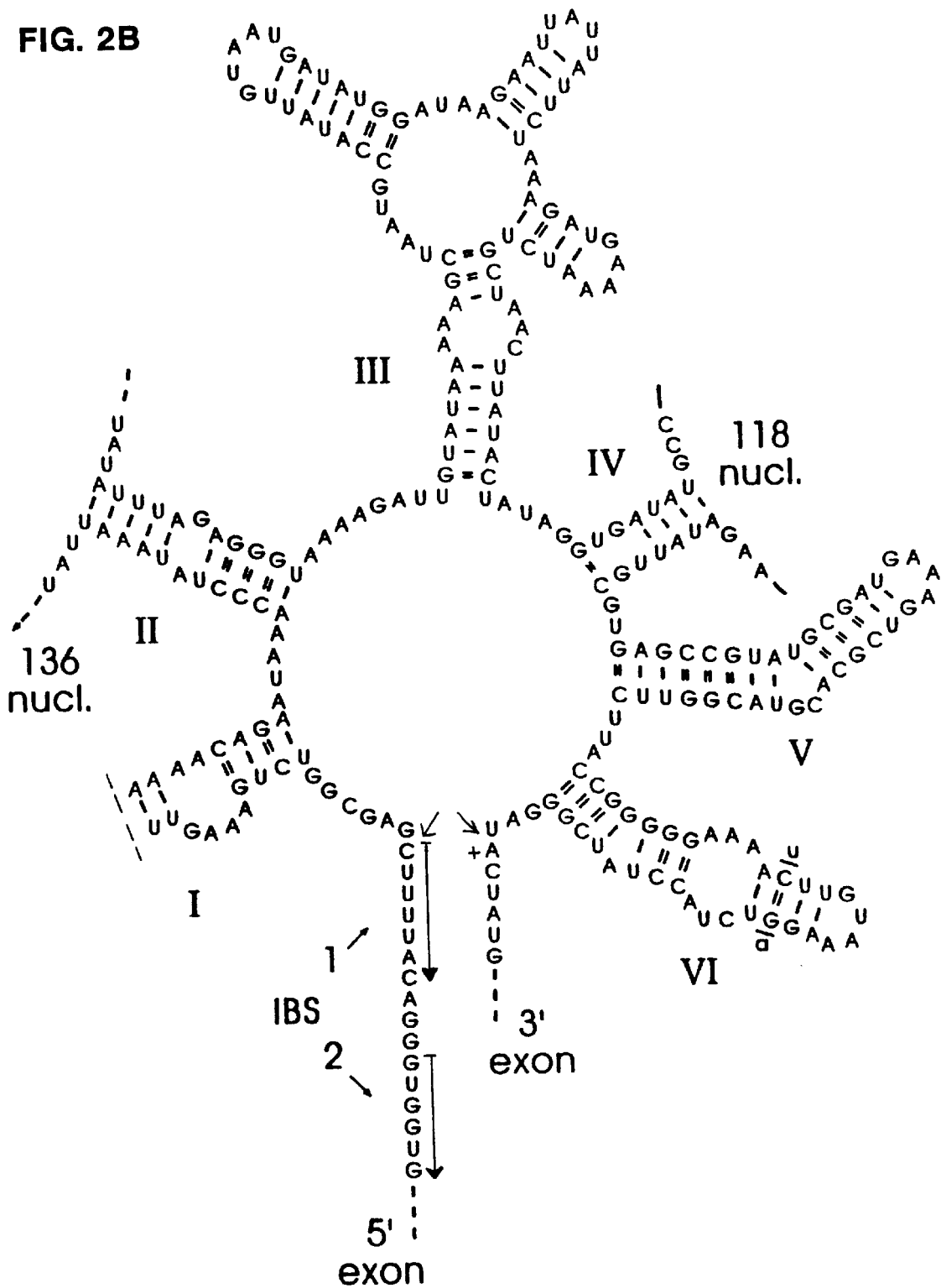
Figure 2C:
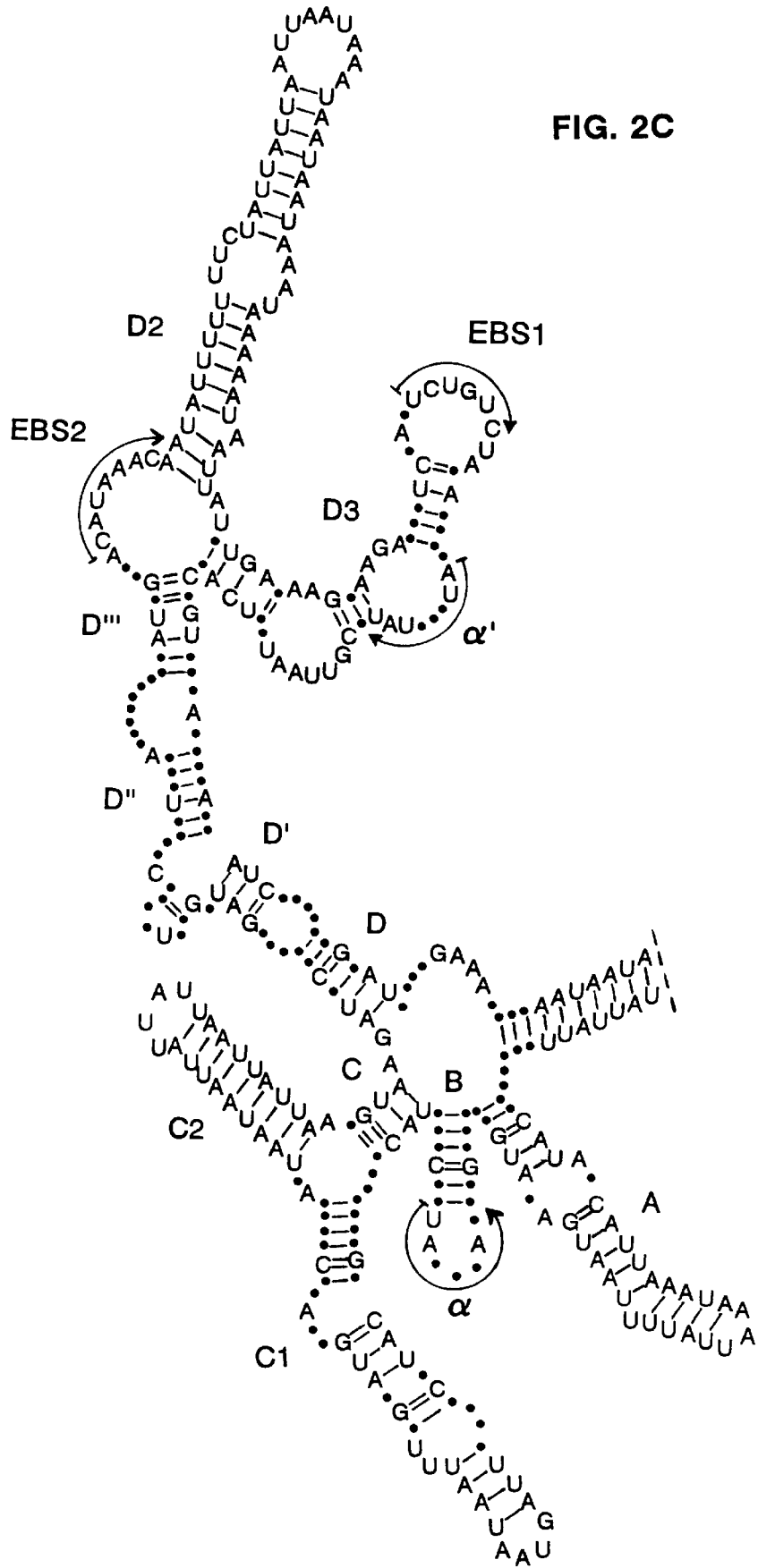
Figure 2D:
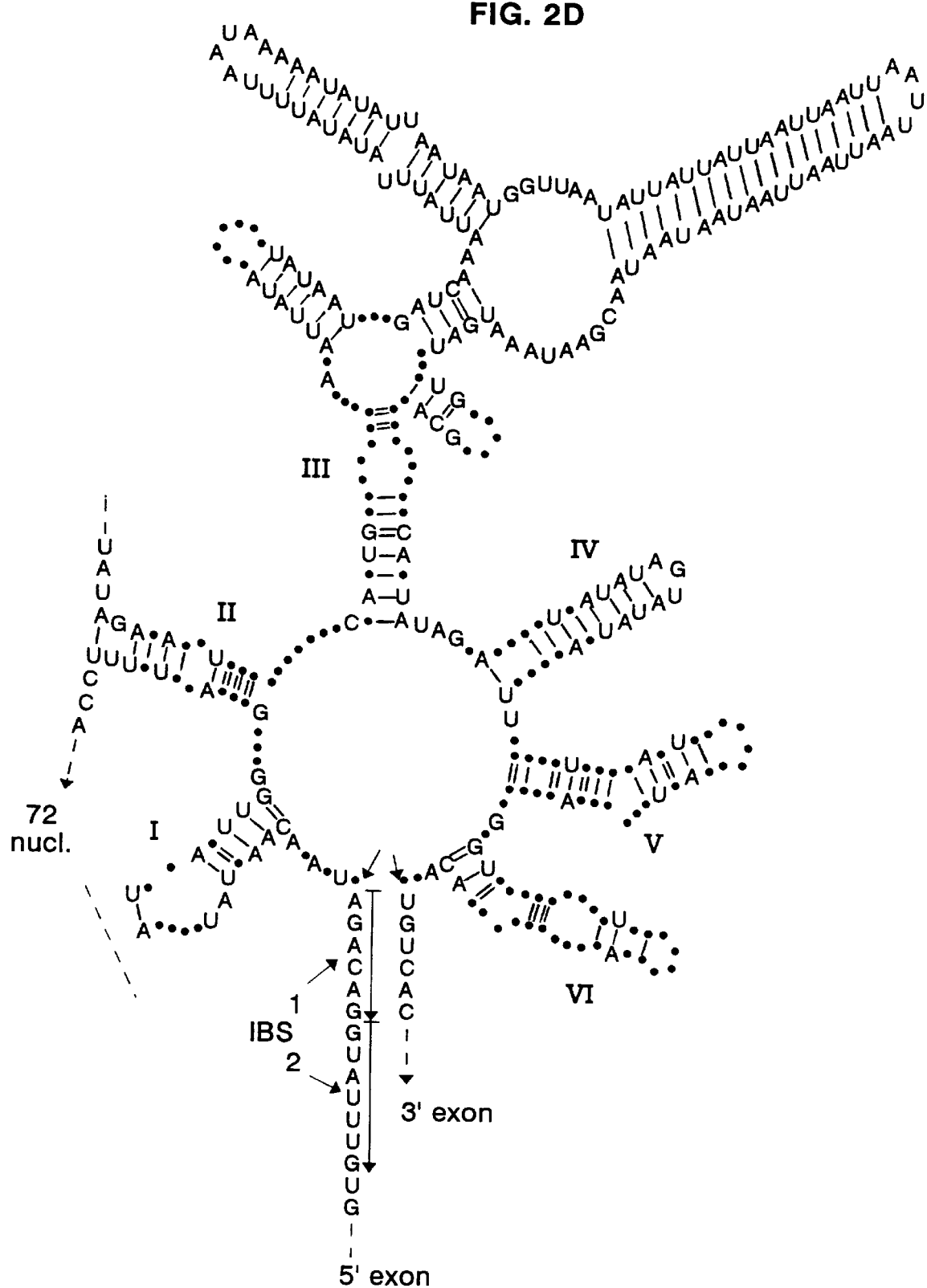
Figure 3:
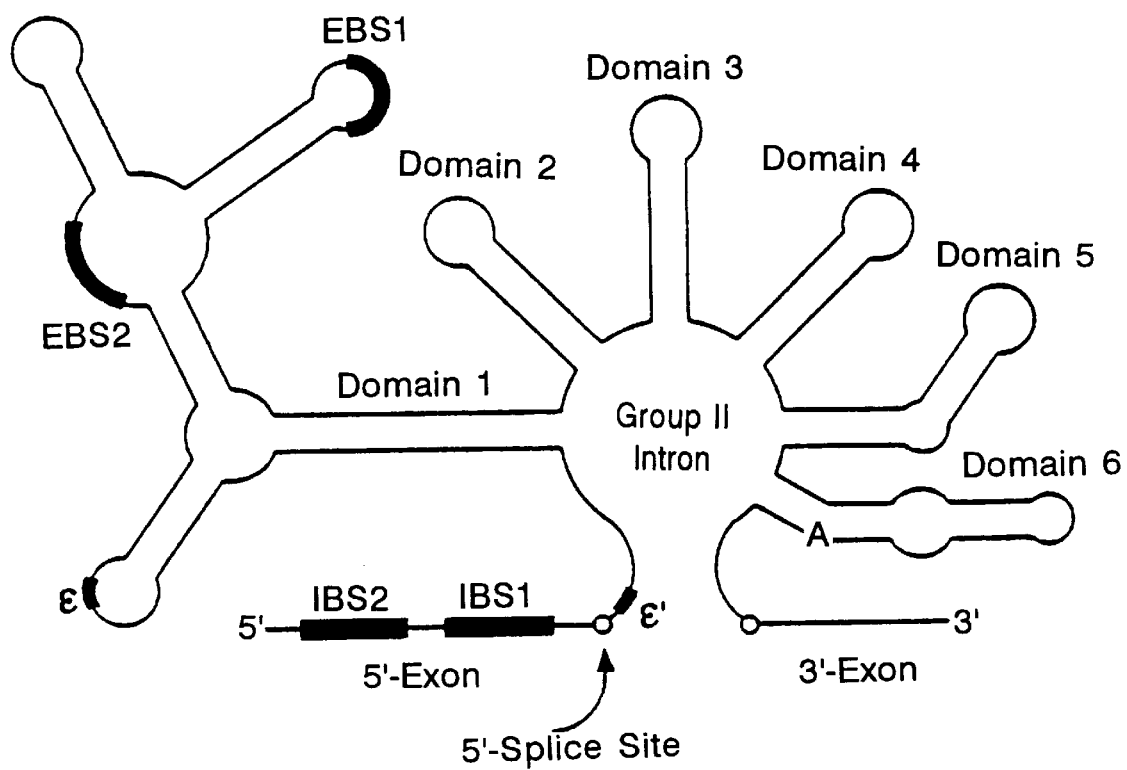
FIG. 3: Shows a schematic of a group II intron. The structure is composed of six subdomains organized like spokes of a wheel. Domain 1 contains the EBS1 and EBS2 regions (Exon-Binding Sites 1 and 2) which base pair to the IBS1 and IBS2 segments of the intron. The first step of splicing is initiated by attack at the 5'-splice site from an adenosine 2'-OH group on Domain 6. Domains 2–4 are dotted because they are dispensable for this first step.

This invention is directed to a composition for catalyzed oligonucleotide cleavage comprising a synthetic non-naturally occurring oligonucleotide compound. The compound comprises nucleotides whose sequence defines a conserved group II intron catalytic region and nucleotides whose sequence is capable of hybridizing with a predetermined oligonucleotide target sequence to be cleaved, such target sequence not being present within the compound. The composition also includes an appropriate oligonucleotide co-factor which may be provided in cis or trans. Preferably, the conserved group II intron catalytic region is a group II intron domain I catalytic region. In one embodiment the conserved group II intron domain I catalytic region may further comprise a conserved portion of a group II intron domain II, a group II intron domain III, a group II intron domain IV, a group II intron domain V, or a group II intron domain VI.

In the composition above, the nucleotides whose sequence is capable of hybridizing with a predetermined oligonucleotide target sequence to be cleaved may be two hybridizing regions, each region having 2 to 12 nucleotides capable of hybridizing with the oligonucleotide target to be cleaved. In one embodiment, each of the regions has 6 or 7 nucleotides. Preferably, the synthetic non-naturally occurring oligonucleotide compound comprises between 80 and 1000 nucleotides. In one embodiment the compound comprises 300–600 nucleotides.

In one embodiment of the invention, the appropriate co-factor is an oligonucleotide compound from a conserved portion of a group II intron domain V having the formula: (SEQ ID NO: 4)

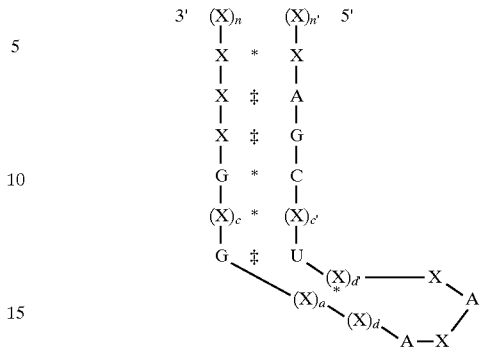

(SEQ ID NO. 3) wherein each X represents a ribonucleotide which may be the same or different; wherein each of $(X)_n$, $(X)_{n'}$, $(X)_c$, $(X)_{c'}$, $(X)_{d'}$, $(X)_a$ and $(X)_d$ represents an oligonucleotide; wherein n, n', c, c', d, d', and a each represents an integer which defines the number of nucleotides in the oligonucleotide with the provisos that n and n' are greater than or equal to 1; a represents an integer which is greater than or equal to 1; d and d' represent an integer which is greater than or equal to 5; c and c' represents an integer which is greater than or equal to 4; wherein each * represents base pairing between the nucleotide located on either side thereof; wherein each ‡ may or may not represent base pairing between the nucleotide located on either side thereof; and wherein each solid line represents a chemical linkage providing covalent bonds between the nucleotide located on either side thereof.

The compositions above may further comprising a divalent cation such as Mg$^{2+}$ or Mn$^{2+}$. Preferably, the predetermined oligonucleotide target sequence to be cleaved is mRNA e.g. a mammalian mRNA, a yeast mRNA, a bacterial mRNA or a viral mRNA. However, the predetermined oligonucleotide target sequence to be cleaved may be DNA. The mRNA may encode a growth factor such as an angiogenic factor, a basic fibroblast growth factor, a colony-stimulating factor 1, cystic fibrosis transmembrane conductance regulator, an epidermal growth factor, an erythropoietin, a fibroblast growth factor, a G-protein, a granulocytemacrophage colony stimulating factor, a growth hormone, IL-1, IL-1R, IL-2, IL-2R, IL-4, IL-6, an insulin-like growth factor, an insulin-like growth factor 1, an interferon, an interleukin, a keratinocyte growth factor, luteinizing hormone receptor, MDR-1, a nerve growth factor, a platelet derived growth factor, a scatter factor, a transforming growth factor α, a transforming growth factor β, a transforming growth factor, or a tumor necrosis factor.

The mRNA may encode an oncogene or a tumor suppressor gene such as bcl-2, bcr-abl, bek, BPV, c-abl, c-fes, c-fms, c-fos, c-H-ras, c-kit, c-myb, c-myc, c-mos, c-sea, cerbb, DCC, erbA, erbB-2, ets, fig, FSFV gpSS, Ha-ras, HIV tat, HTLV-1 tat, JCV early, jun, L-myc, lck, LPV early, met, N-myc, NF-1, N-ras, neu, p53, Py mTag, pim-1, ras, RB, rel, retinoblastoma-1, SV-40 Tag, TGF-α, TGF-β, trk, trkB, v-abl, v-H-ras, v-jun, or WT-1. The mRNA may be associated with a chromosomal translocation or have one or more point mutations. In addition, the mRNA may be an mRNA whose overproduction is associated with a disease or condition.

The mRNA may be a viral mRNA associated with a cytomegalovirus, an Epstein-Barr virus, a hepatitis B virus, a hepatitis C virus, a herpes simplex virus, a herpesvirus, a HIV-1 virus, an immunodeficiency virus, an influenza virus, a papillomavirus, a picornavirus, a polio virus or a T-cell leukemia virus. Alternatively, the mRNA may be a plant mRNA associated with alfalfa, apples, asparagus, bananas, broccoli, carrots, celery, chicory, coffee, cabbage, mustard, corn, cottonseed, squash, cucumber, cantaloupe, grapes, lettuce, palm, potato, rapeseed, raspberry, soybean, sunflower, strawberry, tomato, or wheat.

The invention is also directed to an oligonucleotide transfer vector containing a nucleotide sequence which on transcription gives rise to the synthetic non-naturally occurring compounds above. The transfer vector may be a bacterial plasmid, a bacteriophage DNA, a cosmid, or an eukaryotic viral DNA.

The invention is also directed to host cells transformed by the transfer vector above. The host cells may be prokaryotic host cells or an eukaryotic host cells such as $E.\ coli$, a monkey COS host cell, a Chinese hamster ovary host cell, a mammalian host cell or a plant host cell.

The invention is also directed to a method for cleaving an oligonucleotide comprising the steps of: a) providing a synthetic non-naturally occurring oligonucleotide compound or compounds as defined above and b) contacting the synthetic non-naturally occurring oligonucleotide compound(s) with a target oligonucleotide to cause cleavage of the target oligonucleotide.

A transgenic, non-human vertebrate animal, having one or more cells bearing a DNA sequence encoding the composition above. The transgenic animal may be a mammal such as a cow, goat, sheep, pig, horse, dog, cat, or rodent. In addition, the animal may be a fish, a chicken, or a turkey.

The invention is also directed to a method of treatment which comprises: a) recovering a subject's appropriate cells; b) transforming the cells with a DNA sequence encoding the composition of above; and c) introducing the resulting transformed cells into the subject so as to treat the subject.

Synthetic preparations of mRNA are well known (see Sambrook et al., 1989, *Molecular Cloning: A Laboratory Manual*, 2nd Ed.). Mixed DNA-RNA oligomers with modified base pairs for the ribozyme or minizyme can be prepared by commercially available DNA synthesizers such as those produced by Applied Biosystems, Biosearch, or Milligen for derivatives (Uhlmann, E. and Peyman, A., 1990, Chemical Reviews 90: 543–584.), for H-phosphonate monomers (Agrawal et al U.S. Pat. No. 5,149,798).

The compounds of this invention may be covalently or non-covalently associated with affinity agents such as proteins, antibodies, steroids, hormones, lipids, specific nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the compounds of the present invention may be associated with RNA binding peptides or proteins which may assist in bringing the endonuclease into juxtaposition with a target nucleic acid such that hybridization and cleavage of the target sequence may take place. Nucleotide sequences may be incorporated into the 5' and 3' ends of the group II intron increase affinity for substrates. Such additional nucleotide sequences may form triple helices with target sequences (Strobel, S. A., et al., 1991, Nature 350: 172–174.) which may enable interaction with intramolecularly folded substrate. Alternatively, modified bases within the additional nucleotide sequences may be used that will associate with either single stranded or duplex DNA generating base pair, triplet, or quadruplet, interactions with nucleotides in the substrate.

The compounds of the claimed invention may be further stabilized using methods in the literature for example the use transcription terminators on the 3' end such as the T7 terminator, σ-independent terminator, cry element (Gelfand et al. U.S. Pat. No. 4,666,848) or the TrpE terminator. Furthermore, sequences such as the poly(A) addition signal AATAAA may be added and strategies involving changing the length of the 3' non-coding region (see Gillies, U.S. Pat. No. 5,149,635). These techniques can be used to stabilize RNA in the compound.

The invention also embodies methods of production of the nucleic acid based compounds described above comprising the steps of: (a) ligating into a transfer vector comprised of DNA, RNA or a combination thereof a nucleotide sequence corresponding to said compound; (b) transcribing the nucleotide sequence of step (a) with RNA polymerase; and (c) recovering the compound. The invention also includes transfer vectors, bacterial or phage, comprised of RNA or DNA or a combination thereof containing a nucleotide sequence which on transcription gives rise to the compounds described above.

The invention described herein also provides a method of cleavage of a specific RNA target sequence which comprises reacting the compound with the target sequence so as to thereby cleave the specific target sequence. Such target sequences may be indigenous to mammals or plants. In one embodiment, the target sequence is in a viral gene. The invention also provides a method for the treatment of viral diseases in plants and animals.

Further, many methods have been developed for introducing cloned eukaryotic DNAs into cultured mammalian cells (Sambrook et al., 1989): calcium phosphate- or DEAE-dextran-mediated transfection; polybrene; protoplast fusion; electroporation; and direct microinjection into nuclei. The present invention, however, extends to other means of transfer such as genetic bullets (e.g. DNA-coated tungsten particles, high-velocity micro projectile bombardment) and electroporation amongst others (Maliga, P. (1993) Towards plastid transformation in flowering plants. Tibtech 11: 101–106; Bryant, J. (1992) Transgenic wheat plants: the end of the beginning. Tibtech 10: 342–343.; or Shimamoto, K., Terada, R., Izawa, T., and Fujimoto, H. (1989) Fertile transgenic rice plants regenerated from transformed protoplasts. Nature 338: 274–276.).

Further, the compound described herein may be used in plants to cleave undesirable mRNA. The appropriate cleavage would lead to phenotypic changes. Phenotypic changes in plant cells or plants may include drought resistance, salinity resistance, resistance to fungal, viral or bacterial infection; modifications of growth characteristics; sterility; fruit production; flowering; senescence; altering oil seed metabolic pathways to increase production; and the like (see Shewmaker et al. U.S. Pat. No. 5,107,065). It is evident that one or more RNA involved in determining phenotype are identified, such RNAs may be inactivated by cleavage utilizing the endonuclease of this invention and thus the phenotype of the plant or plant cell altered. Diseases or infections which may be treated in plants with endonucleases of this invention include fungal infection, bacterial infections (such as Crown-Gall disease) and disease associated with plant viral infection.

Phenotypic modifications within animals (including in some applications man) which may be effected by cleaving and thus inactivating target RNAs associated with phenotype would include growth characteristics of animals, fertility, skin/cosmetic modifications, reproductive characteristics, disease resistance and the like. A myriad of applications arise for phenotypic modifications in animals, and plants as previously mentioned. One or more RNAs associated with a given endonucleases may be targeted against such RNAs for their inactivation with consequential phenotypic modification.

Prokaryotic and eukaryotic cell cultures may be phenotypically modified by treatment with endonucleases of this invention. For example, bacterial cultures or yeast cultures involved in production of food components (such as cheese, bread and dairy products) and alcoholic beverage production may be treated so as to modify enzyme content, flavor production, cell growth rate, culture conditions and the like. Eukaryotic and prokaryotic cells in culture may, for example be protected from infection or disease associated with mycoplasma infection, phage infection, fungal infection and the like.

The compounds of this invention may also be used to treat diseases or infection in humans, animals, plants, or prokaryotic or eukaryotic cells. The ability to treat disease or infection is based on the fact that the compounds of this invention are capable of cleaving any RNA which contains a suitable cleavage site. Most RNAs will contain one or more suitable cleavages sites.

The period of treatment would depend on the particular disease being treated and could be readily determined by a physician. Generally treatment would continue until the disease being treated was ameliorated.

Examples of human and animal targets may be bacterial and prokaryotic infection, viral infection and neoplastic conditions associated with the production of aberrant RNAs such as occurs in chronic myeloid leukemia, viruses, growth factors as described above.

The virus may be a plant virus such as a tobamovirus, a tobravirus, a hordeivirus, a potexvirus, a carlavirus, a potyvirus, a closterovirus, a tymovirus, a tombusvirus, a sobemovirus, or a luteovirus. The plant virus may be a potato yellow dwarf virus, a cucumber mosaic virus, a tomato spotted wilt virus, a tomato mosaic virus, a potato virus X (PVX), a potato virus Y (PVY), a carnation latent virus, a tomato rattle virus, a pea early browning virus, a barley stripe mosaic virus, a turnip yellow mosaic virus, a barley yellow dwarf virus, a beet yellows virus, a potato leaf roll virus, a tomato bushy stunt virus, a southern bean mosaic virus, a maize chlorotic virus, beet necrotic yellow vein virus, or a tobacco necrosis virus.

The transgenic organisms described herein may be characterized in that they contain in their genome a sequence which gives rise, on transcription, to the compounds mentioned above. The transgenic organism may be a plant or a non-human mammal. Examples of transgenic mammals include Leder et al. U.S. Pat. Nos. 4,736,866 and 5,175,383; Krimpenfort et al. U.S. Pat. No. 5,175,384; Wagner et al. U.S. Pat. No. 5,175,385; and U.S. Pat. Nos. 5,183,949 and 5,347,075. The transgenic plant, including fruits, and seeds thereof, may be from alfalfa, apple, bean, canola (oilseed rape), cantaloupe, corn, cotton, courgette, cucumber, melon, papaya, pepper, potato, rice, soybean, squash, strawberry, sunflower, sweet pepper, tobacco, tomato, or walnut. Also included are the plant cells transformed by the above-mentioned transfer vector, as well as a prokaryotic or eukaryotic cell, plant or animal, comprising a nucleotide sequence which is, or on transcription gives rise to, the compounds described herein.

An effective amount of a compound of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 $\mu$M to about 500 $\mu$M endonuclease be employed. Compounds comprising nucleotide derivatives, which derivatives may involve chemically modified groups, such as phosphorothioate or methyl phosphonate derivatives may be active in nanomolar concentrations. Such concentrations may also be employed to avoid toxicity.

Therapeutic strategies involving treatment of disease employing compounds of this invention are generally the same as those involved with antisense approaches, such as described in the antisense literature (Chrisley, L. A. (1991) Antisense Research and Development, 1: 65–113; Stein, C. A. et al. Science (1993) 261: 1004–1012). Particularly, concentrations of compounds utilized, methods and modes of administration, and formulations involved may be the same as those employed for antisense applications.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the oligonucleotide, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and oligonucleotides coupled to antibodies directed against tissue-specific receptors, ligands or antigens or coupled to ligands of tissue-specific receptors. Further, specific nucleotide sequences may be added to target the oligonucleotides of this invention to the nucleus, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The oligonucleotides may be encapsulated in a wafer, wax, film or solid carrier, including chewing gums. Permeation enhancers to aid in transport to movement across the epithelial layer are also known in the art and include, but are not limited to, dimethyl sulfoxide and glycols.

For in-vitro use, the compounds of this invention are generally reacted with a target RNA which contains one or more suitable cleavage sites. Optionally, the target RNA may be purified or substantially purified. The nucleotide sequences the compounds of this invention are selected so as to specifically hybridize or form a double-stranded DNA duplex with a target RNA whereafter cleavage takes place. Accordingly, target RNA may be specifically cleaved in-vitro in the presence of other RNAs which themselves would not be cleaved.

The compounds may be utilized in a manner similar to restriction endonucleases, that is for the specific cleavage of RNA to facilitate RNA manipulation. All that is required for such manipulations is that the target RNA to be cleaved contains a uracil base and thus a suitable cleavage site.

The compounds of this invention may be utilized in diagnostic procedures, such as the mapping or fingerprinting of RNA. Specifically, the compounds of this invention would enable mapping of RNA and may be used to detect mutations in RNA sequence. Such procedures may be used in research and may also have forensic and other diagnostic applications.

RNA cleavage products in-vitro may be readily detected, for example, by visualization on acrylamide or agarose gels where the amounts of RNA cleaved are sufficiently large for direct visualization after separation and reaction with nucleotide visualization agents, such as ethidium bromide. Alternatively, where the target RNA cleaved is present in small amounts, such as in a sample containing many RNAs, cleavage products may, for example, be detected by using radiolabelled probes for sequence complementary to the target sequence, or amplification techniques such as PCR (Sambrook et al., 1989).

A target RNA for cleavage in-vitro may be derived from any source, and may be of animal, viral, bacterial, plant, synthetic, or other origin. As RNA is common to all known living organisms, this invention may be utilized to cleave any RNA species having a suitable cleavage site as mentioned previously.

This invention is illustrated in the Experimental Detail sections which follow. These sections are set forth to aid in an understanding of the invention but are not intended to, and should not be construed to, limit in any way the invention as set forth in the claims which follow thereafter.

EXPERIMENTAL DETAILS

A self-splicing group II intron was transformed into a three-part ribozyme that site-specifically cleaves small oligonucleotide substrates with multiple turnover. The multicomponent structure of the ribozyme facilitated quantitation of individual rate constants, interactions between reaction components (5'-exon, Domain 1 and Domain 5), and reaction stereospecificity. The efficient reaction catalyzed by this ribozyme appears to be limited by the chemical rate of hydrolysis. An Rp phosphorothioate substrate may be the preferred diastereomer of the ribozyme.

Self-splicing group II introns are essential for the processing of many organella genes in plants and yeast (Umesono, 1989; Kuck, 1990). Group II introns are characterized by a conserved secondary structure that can be organized into six domains. The splicing reaction is initiated by attack of a 2'-hydroxyl group projecting from the bulged adenosine of Domain 6 (D6), which attacks the 5'-splice site and generates a "lariat" intermediate (Peebles, 1986; van der Veen, 1986).

In group II introns, both steps of splicing can proceed if the initial nucleophile is a water molecule rather than the 2'-OH of a bulged adenosine in D6 (Jarrell, 1988 (a); Jarrell, 1988 (b); van der Veen, 1987). In addition, hydrolysis promotes the apparent first step of group II intron trans-splicing by 5'-exon-G oligonucleotides (Jacquier, 1986; Altura, 1989). Domain 5 (D5) is the most phylogenetically conserved region of the group II intron and it has been observed to act intrans, promoting specific hydrolytic cleavage tat the 5'-splice site (Jarrell, 1988). It is clear that D5 and Domain 1 (D1) are absolutely required for the first step of splicing (Koch, 1992). Recent kinetic analysis have examined the hydrolysis of 5'-exon from domains 1–3 when D5 is provided in-trans (Franzen, 1993; Pyle, 1994). These studies showed that D5 associates with high affinity (~300 nM) to the other active site components. The strength of D5 binding is especially surprising considering that this small RNA (~40 nts) is largely duplex in form and, having no apparent phylogenetic covariation with the rest of the intron, seems to bind without the aid of base-pairing interactions. This D5-catalyzed reaction obeys a straightforward Michaelis-Menten mechanism in which the chemical step of hydrolysis appears to be rate-limiting (Pyle, 1994).

Figure 4A:
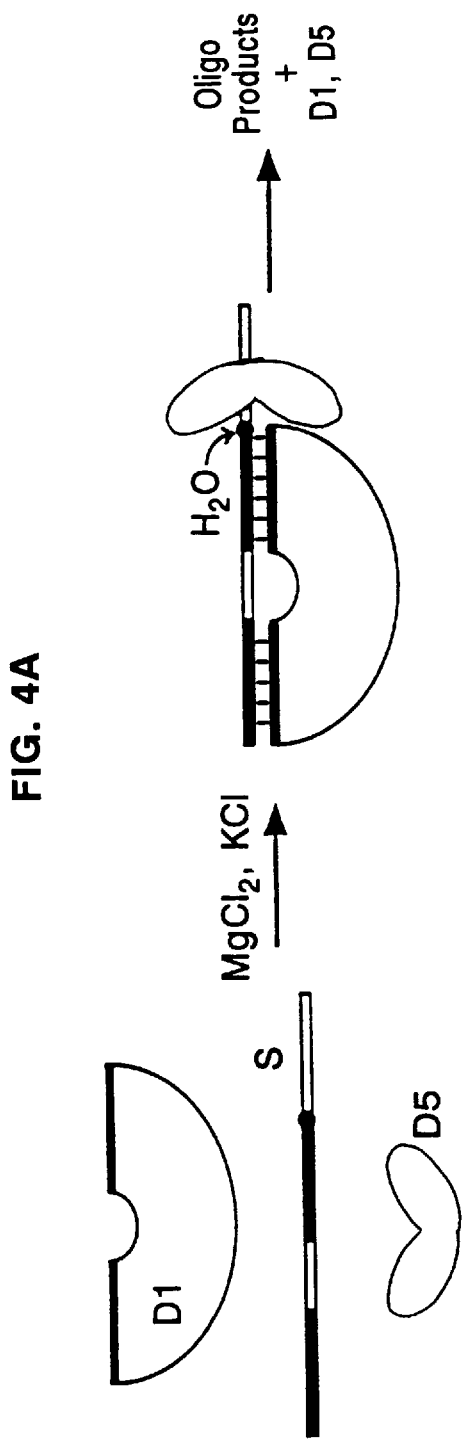
FIGS. 4A and 4B: Cleavage of a short RNA substrate (S) by the group II ribozyme.

In order to independently evaluate the role of D1, D5 and 5'-exon sequences on active-site folding and catalytic activity, we constructed a modular group II intron ribozyme consisting of a 425 nt Domain 1 RNA (D1) that binds small oligonucleotide substrates (s, 24–27 nts) in trans. Efficient cleavage at a single site is promoted by addition of a reaction cofactor (D5, 58 nts) that is also provided in trans (FIG. 4a). This ribozyme is analogous to the Tetrahymena ribozyme except that the cofactor is a short RNA which is unchanged in the reaction instead of a nucleophilic guanosine that is consumed during reaction (Zaug, 1986 (a); Zaug, 1986(b); Pyle, 1994). With the reaction substrate and co-factors cleanly separated, it is now possible to hold any one component rate limiting in order to determine its precise role in binding or catalysis. The modular structure permits facile incorporation of mutations and single-atom changes for probing mechanism (Cech, 1992). We have used this true ribozyme to begin construction of a more complete kinetic framework for group II intron catalysis and to determine the stereospecificity of a reaction analogous to the first step of group II intron self-splicing.

Figure 4B:
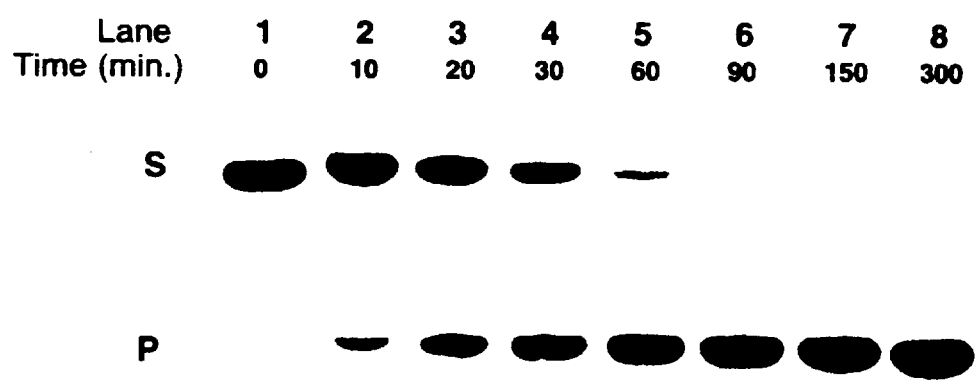

Kinetics of Substrate Cleavage by the Ribozyme: The reaction substrate (S) is a small oligonucleotide with a sequence analogous to the 5'-exon/intron boundary in the ai5g group II intron (FIG. 4a). In the presence of D1 and D5, this oligonucleotide is cleaved specifically at the CpG sequence that corresponds to the normal 5'-splice site (FIG. 4b). If either D1 or D5 is absent from the reaction, no cleavage of the substrate occurs. Previous studies showed that a 52-nt 5'-exon terminating in the CpG cleavage site was the minimal substrate necessary for trans-splicing or trans-cleavage by the ai5g group II intron (Jacquier, 1986; Jacquier, 1987). In our study, only 17 nts of exon, encompassing both IBS1 and IBS2 (FIG. 4) were required for efficient cleavage. This substrate also contains 7–8 nucleotides of intronic sequence, including nucleotides (+3 and +4) involved in the ∈—∈' interaction believed to stabilize 5'-splice-site association (Jacquier, 1990).

$K_{ms}$ $k_{max}$ and $k_{max}/K_m$ values for S were obtained using single-turnover kinetics where $[S] \ll K_{ms}$ and [D5] was saturating relative to [D1] (Table 1, line 1) according to standard kinetic procedures (FIG. 5, Table 1, line 1) (Pyle, 1994; Herschlag, 1990; Fedor, 1992). $K_m^s$ determined from this plot is 6.3 Nm, implicating strong association between S and D1 (see IBS/EBS pairings, FIG. 4a). This is the first quantitative analysis of the strength of binding between the 5'-exon and D1, and the $K_m^s$ approximates a dissociation constant for the IBS/EBS pairings plus any other interactions mediating intron/exon association. At very high concentrations of D1 (the plateau of the plot in FIG. 5A) $k_{obs}$ reflects the conversion of E.S→E.P, where E represents D1 that is fully saturated with D5 cofactor and P represents reaction products. Under these saturating, single-turnover conditions, the apparent rate (defined here as $k_{max}$) represents the rate of the chemical step and any conformational changes that take place within the E.S complex. The $k_{max}$ value at saturating [D1] was 0.021 min$^{-1}$.

For conditions under which [D5] was rate-limiting, values for $K_m^{D5}$, $k_{max}^{D5}$ and $k_{max}/K_m^{D5}$ were determined by monitoring the cleavage rate of S in the presence of saturating D1 through a range of D5 concentrations (FIG. 5C, Table 1, line 3). In this case, each molecule of S was bound to D1 and overall rate was limited by the concentration of D5. The $k_m^{D5}$ is 870 nM, $k_{max}/K_m^{D5}$ is 2.2×10$^4$ M$^{-1}$min$^{-1}$ and $k_{max}$ is 0.019 min$^{-1}$. Values of $k_{max}$ from both D1 and D5-limited experiments are in close agreement (Table 1). The consistency of the data obtained under limiting D1 and D5 conditions suggests that under either condition, reaction proceeds through the same ternary complex for which the individual components have different affinities.

Specific, efficient cleavage of small substrates by the group II ribozyme has now been observed in a kinetically characterized system. The results are consistent with kinetic behavior of larger, more complex constructs of the group II ribozyme has now been observed in a kinetically characterized system. The results are consistent with kinetic behavior of larger, more complex constructs of the group II intron (Jarrell, 1988; Pyle, 1994). The ribozyme construct can now be used to carry out detailed enzymological studies that examine reaction mechanism at an atomic level. Of particular interest is the stereospecificity of group II catalysis of the first and second steps of splicing (Lamond, 1993; Moore, 1993(a); Moore, 1993(b)). Group II introns are invoked as an autocatalytic model for the spliceosome and there are indications that group II introns and pre-mRNA splicing share a common evolutionary ancestry (Cavalier-Smith, 1991).

Figure 6:
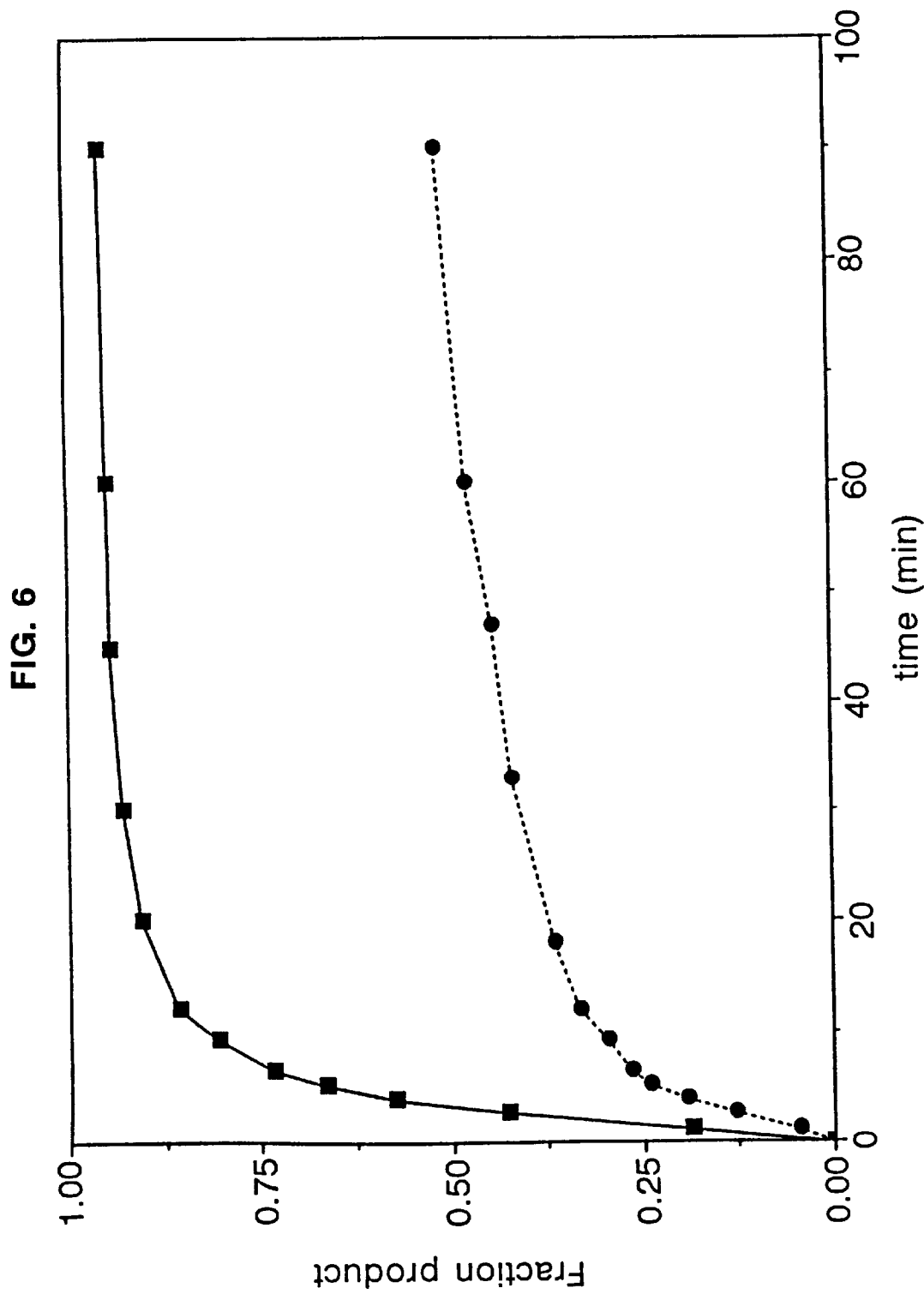
FIG. 6: Ribozyme cleavage of a single phosphorothioate linkage: Comparison of ribozyme cleavage of a transcribed all-phosphate RNA substrate (squares: connected by - - -) and a synthetic substrate containing a single phosphorothioate at the cleavage site (circles; connected by - - -). A standard ribozyme digestion was performed as in FIGS. 4 and 5A & B, except that, unlike these previous kinetic figures, final [KCl] was 2M in order to approach endpoint more rapidly. Doubling the KCl concentration increases the rate of reaction approximately ten-fold, while pseudo-first order plots remain linear (data not shown). The all-phosphate substrate was cleaved to 96%±0.8% (with 95% confidence and 4 trials), empirically determined after >7 half-times. This substrate was cleaved 52%±4% (with 95% confidence and 5 trials) at >7 half-times (see FIG. 7, lane "M"). Time-courses using newly synthesized RNA reproducibly resulted in endpoints slightly less than 50%. Phosphorothioate linkages slowly convert to phosphates during storage and this factor may explain why slightly more than 50% of the substrate is cleaved (Herschlag, 1991). Time-courses using this oligonucleotide after it was first synthesized were cleaved to <48%. Including 10 mM DTT in the reaction had no effect on the extent of cleavage (data not shown).

Stereospecificity of Cleavage by a group II Ribozyme: Synthetic incorporation of a chiral phosphorothioate linkage results in an equal mix of Rp and Sp diastereomers. A synthetic substrate for the ribozyme was machine-synthesized, containing a single phosphorothioate linkage at the cleavage site. The ribozyme cleaves this substrate to an endpoint of ~50%, suggesting that it has a preference for one of the two diastereomers (FIG. 6). However, the fraction uncleaved by the ribozyme could represent RNA that is unreactive for other reasons, such as the presence of protecting groups left over from chemical synthesis. To determine the stereochemical identity of the fraction uncleavable by the ribozyme, the uncleaved fraction was gel-purified and examined by digestion with snake venom phosphodiesterase (SVPD). SVPD is a 3'→5' exonuclease that readily cleaves phosphate and Rp phosphorothioate linkages. This enzyme is markedly inhibited by Sp phosphorothioates, cleaving them 2000× more slowly than their corresponding Rp isomers (Burgers, 1979). When a 5'-end labelled RNA contains an internal Sp phosphorothioate linkage, SVPD will readily digest the 3'-end of the strand and suddenly pause at the site immediately adjacent to the Sp linkage (+1 G). This apparent stall will accumulate and then diminish at long times as the SVPD slowly cleaves through it and then rapidly digests the remaining strand to mononucleotides.

Figure 7:
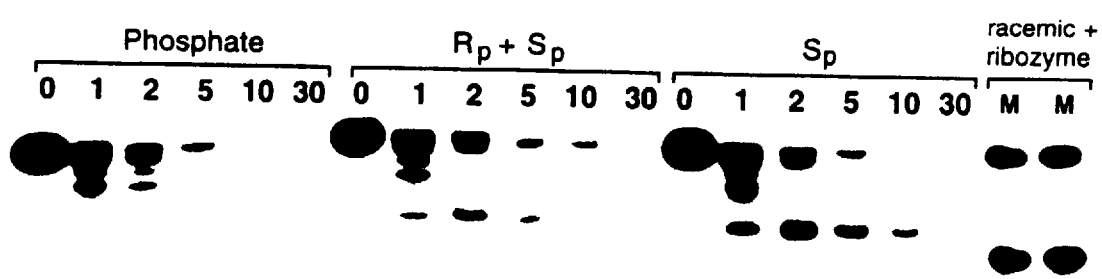
FIG. 7: Determining the stereochemical identity of the less reactive substrate. Three different synthetic substrates (0.4 nM) were digested with 3 U/μl of snake venom phosphodiesterase (SVPD, Boehringer-Mannheim), in a reaction containing 0.1 μg/μl carrier tRNA, 50 mM Tris-HCl pH 8.5 and 10 mM MgCl$_2$. Incubations were at 37° C. for 0, 1, 2, 5, 10 and 30 minutes, respectively. The lanes marked "phosphate" represent digestion of a normal all-phosphate substrate (described in FIGS. 5A & B). The lanes marked "Rp+Sp" are digestions of a synthetic substrate containing a single phosphorothioate at the cleavage site (described in FIG. 6). The lanes marked "Sp" are digestions of the synthetic phosphorothioate substrate that was less reactive in the presence of the ribozyme. To isolate this substrate, the racemate (Rp+Sp) was cleaved to apparent completion by the ribozyme (as in FIGS. 9A & B), resulting in the 50% cleavage shown in lane 'M". The less reactive band was re-isolated by PAGE and purified in the same manner as the other two substrates before treatment with SVPD. Radioactive counts were quantitated and the amount of stalling at +1 G was expressed as a fraction of the whole lane. This stall product fraction was integrated over the timecourse of the reaction to give relative amounts of exo-nucleolytic stalling between the three time courses. The two reactions (Rp+Sp and Sp) that had not reached full digestion by 30 min. were extrapolated to theoretical endpoints using the slope of the last two time points. Both substrates gave extrapolated endpoints of 42 min. The final ratio of stall product at +1 G was {0.05:0.59:1} for {phosphate:Rp+Sp:Sp}, respectively.

Three 5'-end labelled RNAs were subjected to cleavage by SVPD (FIG. 7). An all-phosphate substrate was readily digested, with no apparent stalling at position 18, adjacent to the ribozyme cleavage site (FIG. 7, phosphate panel). Digestion of the racemic substrate (never treated with ribozyme) resulted in prominent exonucleolytic stalling adjacent to the single phosphorothioate incorporated at the ribozyme cleavage site. After incubating the racemic substrate with ribozyme (for >7 reaction half-times), the ribozyme-uncleavable fraction was digested with SVPD to yield a predominant stall product that was much greater in intensity than observed for the racemic mix (FIG. 7, Sp panel). For each lane, the number of counts in the stall band were normalized for the total number of counts in the entire lane (from 1→24 nts). Using this value, we calculated the integrated population of the stall product over the duration of the timecourses shown. The integrated intensity of the stall product in the "Sp" panel (FIG. 7) was 1.0 relative to the integrated intensity of 0.59 in the racemic "Rp+Sp" panel. An integrated intensity 0.05 for the "phosphate" panel may be taken as a measure of background. Together with the fact that the racemic substrate is cleaved by the ribozyme to ~50%, these results suggest that the group II ribozyme may preferentially cleave the Rp diastereomer.

Taking into account the 50% endpoint for cleavage of the mixed substrate, rate constants for cleavage of the phosphorothioate substrate were readily obtained (Table 1). A two-fold diminution in rate (the "thio-effect") was observed for cleavage of a phosphorothioate linkage. The magnitude of this rate-decrease, upon substitution of phosphate with phosphorothioate, has been cited as evidence for a reaction rate limited by chemistry rather than conformational changes (Herschlag, 1991). This would be consistent with results from previous studies of 5'-splice-site hydrolysis by a two-piece ribozyme. Correspondence between multiple-turnover and single-turnover kinetic parameters, together with the observations that $K_m^{D5} \approx K_d^{D5}$ and that rate was log-linear with pH led to the hypothesis that the reaction was limited by the chemical rate of hydrolysis (Pyle, 1994).

Figure 8A:
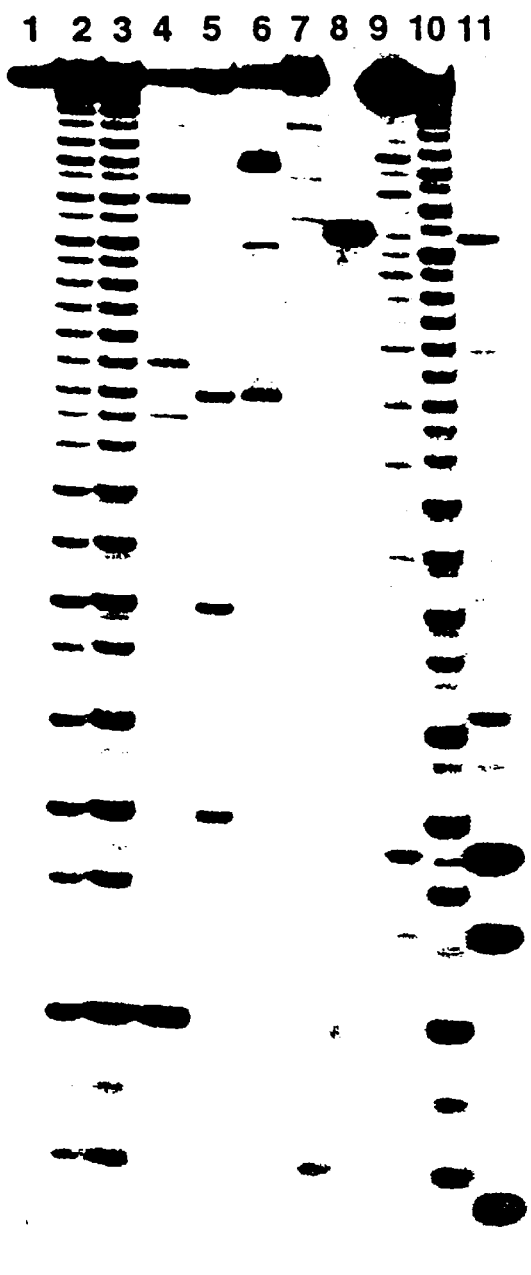
FIGS. 8A and 8B: Nuclease mapping of transcribed substrates and their cleavage products.
Figure 8B:
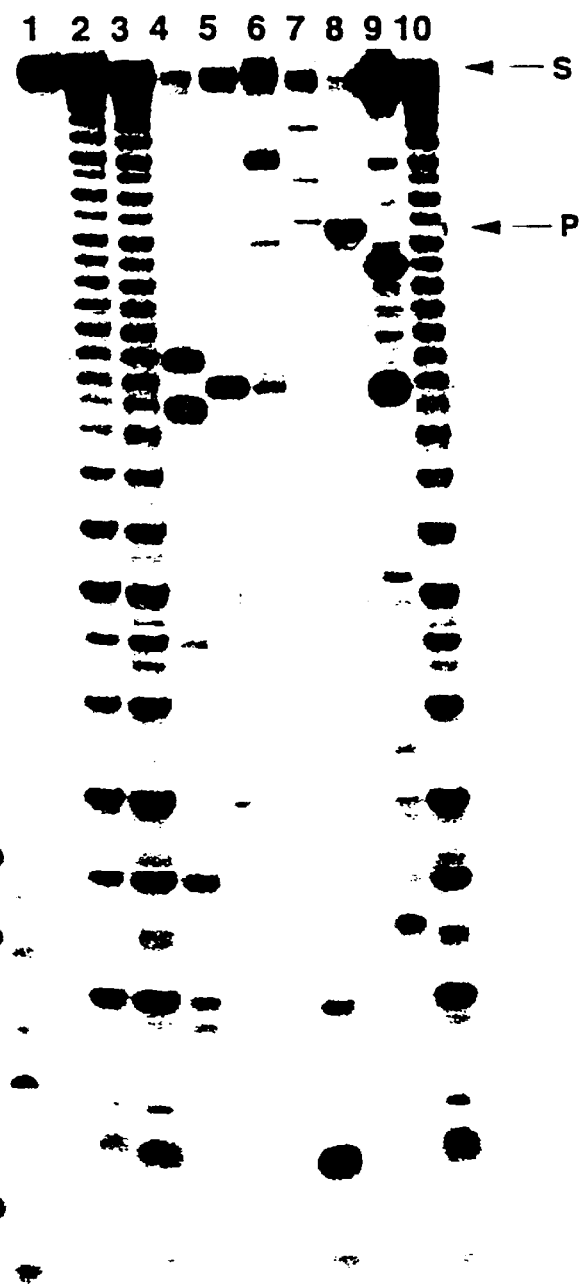

In order to directly test the hypothesis that the ribozyme cleaves an Rp diastereomer, a new substrate was prepared by in-vitro transcription. T7 RNA polymerase incorporates only Rp phosphorothioates into RNA polymers (Griffiths, 1987). Using α-thio-GTP, we transcribed an RNA substrate containing an Rp phosphorothioate at every G residue, including the 5'-splice site (5'SS). Just as the ribozyme specifically cleaves a phosphodiester linkage at the 5'SS sequence (FIG. 8, lane A8), the ribozyme specifically cleaves a substrate containing an Rp phosphorothioate linkage at the cleavage site (FIG. 8, lane B8). To confirm that the ribozyme cleaves both phosphodiester and phosphorothioate RNA substrates uniquely at the 5'SS sequence, the transcribed substrates and products were mapped with a battery of sequence- and stereo-specific nucleases (FIG. 8, lanes 4–7, 9). The substrate containing all-phosphate linkages was mapped next to the substrate containing phosphorothioates at G resides (FIG. 8, Sections A and B). The proper sequence at the cleavage sites was confirmed by digestion of substrates with C13, B-cereus and T1 endonucleases (Boguski, 1979; Donis-Keller, 1977). Product oligonucleotides migrate at the expected position relative to specific nuclease cuts at −1 C and +1 G on the substrates. The endonucleolytic digests described above, together with U2 digestion, confirmed the absolute sequence throughout both substrates (FIG. 8). The migration of the ribose product with a 19-mer P1 endonuclease digestion product suggests that the group II ribozyme leaves 3'-OH and 5'-phosphate termini. The presence of a phosphorothioate at the cleavage site was confirmed by a gap in the P1 nuclease ladder of the thio-substrate (lane 9), together with $I_2$ cleavage of the thio-substrate ($i_2$ data not shown) (Potter, 1983; Schatz, 1991). Taken together, these data show that the ribozyme is selecting the proper cleavage site on both ribose and phosphorothioate-containing substrates. Thus, the ribozyme readily cleaves the Rp diastereomer of a transcribed substrate and does not select adjacent phosphate sites for attack.

Even though the ribozyme specifically cleaves transcribed substrate at an Rp phosphorothioate, the partial digests do not provide quantitative evidence that the substrate sequence and linkage sulfur content are homogeneous at that site. Significant de-thioation at the splice-site linkage would result in conversion to phosphate and apparently efficient cleavage by the ribozyme. We sought a quantitative demonstration that the group II ribozyme cleaves a linkage that is uncleavable by P1 endonuclease. To address these concerns, the thio-substrate was transcribed in the presence of $\alpha$-$^{32}$P-CTP. Because P1 endonuclease cannot cleave RP phosphorothioates, a total P1 digest of this substrate leads to three products in approximately equimolar ratios: *pC, *pCp$_s$G and *pCpsGp$_s$G where p$_s$ indicates a phosphorothioate linkage (FIG. 9A, lane 3). Because the intensity of the three bands are approximately equimolar, this indicates that the substrate has been faithfully transcribed by T7 RNA polymerase and that the cleavage site dinucleotide must be an Rp linkage with the same level of phosphorothioate incorporation as positions +5 G and +6 G (which end up in the trinucleotide). When a sample of internally $^{32}$P-labelled substrate is cleaved to completion by the ribozyme and then immediately digested with P1 under similar conditions, two predominant bands are observed: *pC and *pCp$_s$Gp$_s$G (FIG. 9A, lane 4). The middle p*Cp$_s$G band, corresponding to the ribozyme cleavage site, is considerably diminished in intensity while the *pC band is enhanced. Incubation of substrate with d1 or D5 alone, followed by P1 digestion does not result in a diminution of the middle *pCp$_s$G band (FIG. 9A, lanes 4+5). These results quantitatively demonstrate that this group II ribozyme cleaves an Rp phosphorothioate in a transcribed substrate that is homogeneous in sequence and linkage at the cleavage site.

Figure 9B:
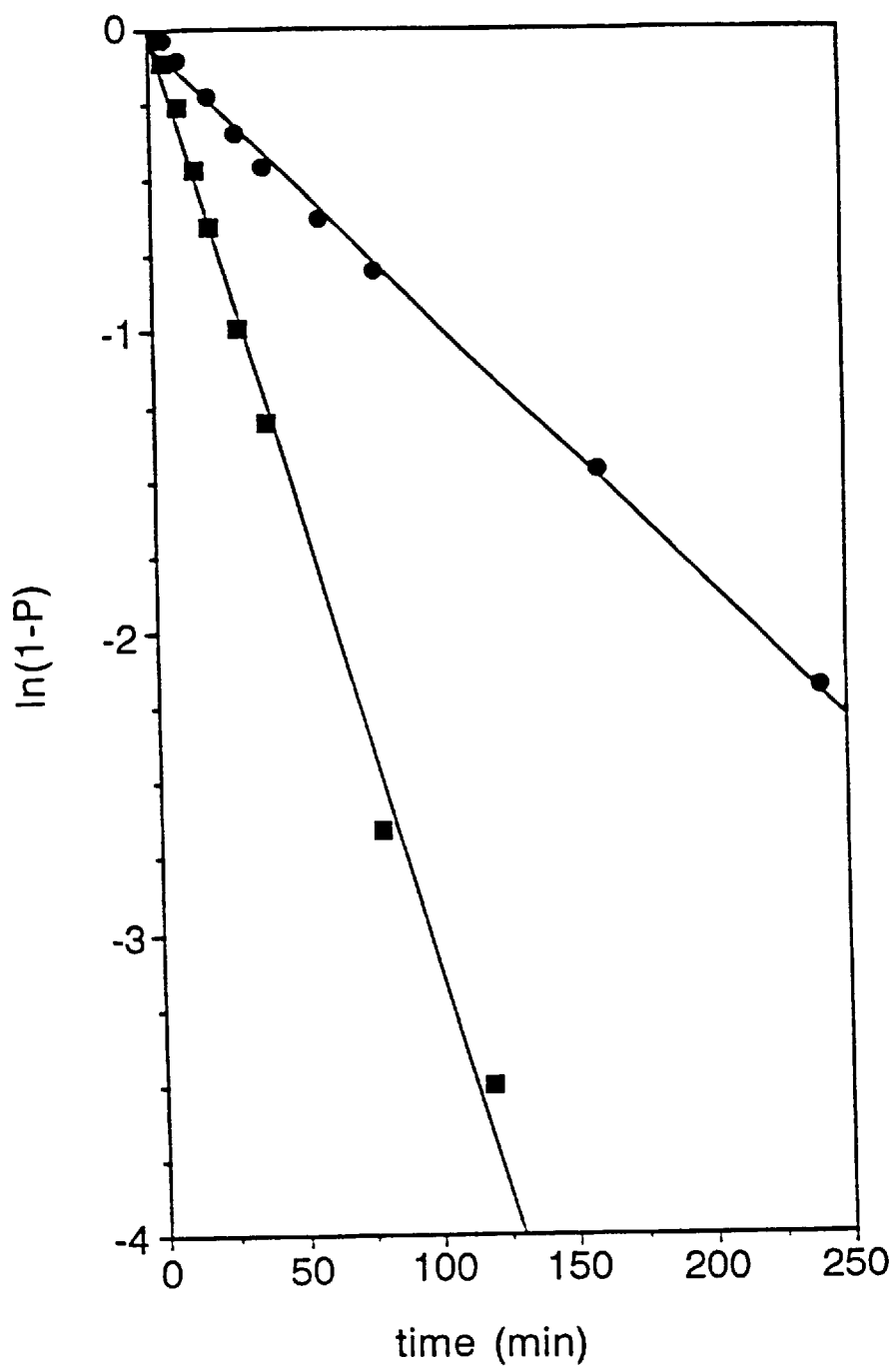

For the transcribed phosphorothioate substrate, the cleavage kinetics were quantitated at D1 and D5 saturation, resulting in an apparent $k_{max}$ value approximately 3-fold slower than that of a phosphate at the ribozyme cleavage site (FIG. 9B). Like the "thio-effect" observed using synthetic substrates, this value is consistent with an apparent rate-limiting chemical step (Table 1, column 7). The rate of cleavage in this homogeneously Rp case is the same (within error) as that of the 50% synthetic substrate that is cleavable by the ribozyme. This provides further evidence that the cleaved fraction in the synthetic experiments is predominantly Rp in configuration.

The new group II ribozyme described here has provided a quantitative description of inter-domain interactions, individual rate constants and reaction stereospecificity. This is the first example of a group II intron that has been transformed into a ribozyme construct that catalyzes an efficient, single reaction on small oligonucleotide substrates. The ribozyme acts as a sequence-specific RNA endonuclease and consists of two RNA subunits which are essential for catalysis. Kinetics for the reaction are unusually clean and suggest a stable, homogeneous combination of reaction components. Like the Tetrahymena ribozyme, the design of this group II construct facilitates biochemical and kinetic studies required for identification of active-site residues and tertiary interactions involved in catalysis.

The new three-part system shows that interactions between Domain 1 and the 5'-exon are very strong and that the EBS-IBS pairings plus the first several intronic nucleotides are all that is required for 5'-splice site recognition in this reaction. Although compensatory base substitutions have been performed, this is the first study to quantitate the magnitude of 5-exon binding to the intron (~6 nM) (Jacquier, 1987). The $k_{cat}/K_m^s$ value for this ribozyme, ($3.3 \times 10^6$ M$^{-1}$ min$^{-1}$) is ~20× slower than that of the Tetrahymena ribozyme, which is rate-limited by duplex association rather than chemical or conformational steps (Herschlag, 1990). A slow chemical step (0.02–0.1 min$^{-1}$) appears to limit the rate of RNA hydrolysis by ai5g group II ribozymes and as a result, $k_{max}/K_m$ is slower than the rate of duplex formation. The results using this construct confirm that the interaction of D5 with the other components is very strong, especially given the ill-defined nature of its tertiary interactions. The kinetic parameters describing the kD5-dependent reaction are similar in this three-part system to those in a related tow-part system that included D2 and D3 and covalent attachment of 5'-exon to D1 (Pyle, 1994). However, the 2× higher [KCl] used here stimulates the rate in both systems by 2–3-fold.

The ribozyme construct described here is relevant to splicing because a hydrolytic first step does not prevent the second step from occurring (Jarrell, 1988; and van der Veen, 1987). Furthermore, the first step is believed to be rate-limiting in two-step splicing by the ai5g group II intron and the rate of reaction by our ribozyme is comparable to that of overall splicing under similar reaction conditions (Jarrell, 1988; Pyle, 1994; Jacquier, 1987; Peebles, 1987; Chanfreau, 1994; and Peebles, 1993). The results observed here are not unique to the KCl conditions known to promote 5'-splice site hydrolysis. Efficient trans-cleavage of the small substrate occurs if KCl is replaced with any of other monovalent salts previously reported to promote the full splicing reaction.

Our results demonstrate that a group II ribozyme preferentially cleaves an rp diastereomer at the 5'-splice site in a reaction that appears to be analogous to the first step of splicing. There are several possible interpretations of this result, given that there are two distinct D5-catalyzed reactions that involve formation of the EBS-IBS pairings (Suchy, 1991). One possibility is that our system mimics the forward first step of splicing and that group II introns generally proceed with Rp stereospecificity during the first step. If this is so, it is remarkable given that spliceosomal processing (for which group II introns are commonly invoked as models) proceeds with Sp stereospecificity during the first step (Moore, 1993; Maschhoff, 1993). It has been proposed that Rp stereospecificity, in either step of group II splicing, would indicate that group II introns are unrelated to the spliceosomal apparatus (Lamond, 1993). However, it is possible that hydrolysis reactions or reactions where the substrate is presented in-trans may result in different stereospecificity than that of cis-splicing. This might occur if the ε—ε' interaction (between the +3, +4 and +116, +117 nts of ai5g) cannot form properly in-trans or if branch formation requires participation of additional subunits not present in our construct. In any case, we have characterized a minimal first step reaction which proceeds with comparable rates and subunit binding constants to those of more complicated systems and is specific for cleavage of sequences immediately surrounding the 5'-splice site. Thus, if stereospecificity of our system turns out to be different than that in cis-splicing, it means that we can build on our system to identify additional structures solely responsible for Sp branch formation. It would remain relevant to pre-mRNA splicing because snRNAs are believed to have evolved from group II domains that became separated and started to function in-trans, much like our system (Sharp, 1985; Cech, 1986). It is therefore important to understand how the group II intron can be faithfully divided into trans-ribozyme constructs.

A second possibility is that our system mimics a reversal of the second step of splicing and that the reaction may not proceed through the same active site as that utilized for branch formation. There are many indications that a reaction equivalent to the reverse of the second step of group II splicing can result in hydrolysis of linkages that follow 5'-exon sequences, particularly when certain structural features are lacking or under alternative reaction conditions (Jarrell, 1988; Suchy, 1991). However, there are several indications that our reaction is not a reversal of the group II intron second step. D3 has previously been shown to be important for spliced exon-reopening, independent of its role in efficiency of the first step (Koch, 1992; Bachl, 1990). Our construct does not contain D3. Perhaps most importantly, our ribozyme does not readily cleave an oligonucleotide composed of ligated exons (nts –19 to –1 of 5'exon followed by the first 9 nts of the 3'-exon, data not shown). When provided in excess, this oligonucleotide is significantly less inhibitory to our reaction than an equal amount of 5'-splice-site substrate, thus implicating effects on both binding and chemistry. Therefore, the intronic sequences of our normal substrate are important for catalysis (perhaps verifying the importance of the ε—ε' interaction) and our reaction mimics the forward first step in both sequence specificity and kinetic profile.

In addition, like the first step of splicing this reaction is inhibited by the presence of a C residue immediately 3' to cleavage site.

Relationship to group II intron self-splicing:

The ribozyme described here behaves in a manner consistent with the first step of group II self-splicing and therefore serves as a representative model for first step processes (Table 2). The fact that the reaction proceeds hydrolytically, rather than through branch-point attack, does not exclude the reaction from representing the first step for several reasons. The first step of splicing can proceed by hydrolysis without preventing the second step from occurring (van der Veen et al., 1987; Jarrell et al., 1988(b)). Therefore, the hydrolytic first step is a significant catalytic strategy that group II introns can exploit in order to effect splicing. Spontaneous attack of water at specific internucleotide linkages is not a favorable process in the absence of a catalyst. The uncatalyzed rate for hydrolytic cleavage of the phosphodiester linkage has been estimated to be $3 \times 10^{-9}$ min$^{-1}$ (Herschlag and Cech. 1990). Given the kinetic parameters reported here, the group II intron provides a $1 \times 10^{7}$-fold rate-enhancement for hydrolytic cleavage at the 5'-splice site. Like RNase P, the group II intron contains active site functionalities that specifically promote this reaction. Recent studies of in-vitro self-splicing show that, under all reaction conditions, the first step continuously proceeds through both competing hydrolytic and transesterification pathways. It is well documented that the first step of self-splicing is rate-limiting in ai5g group II intron (Jacquier and Michel, 1987; Peebles et al., 1987; Chanfreau and Jacquier, 1993). Therefore, concrete kinetic parallels link the ribozyme reported here and the overall rate of group II intron self-splicing.

The reaction reported in this study might be considered analogous to the "spliced-exon-reopening" or SER reaction promoted by group II introns in high concentrations of KCl. This is unlikely given that ligated exons are a poor substrate for the ribozyme and that our results are not unique to the KCl conditions exclusively thought to promote SER (Jarrell et al., 1988(b)). Efficient trans-cleavage of the small substrate occurs if KCl is replaced with any of other monovalent salts previously reported to promote the full splicing reaction. Another distinguishing feature is that the SER reaction is unaffected by C substitution at the +1 nucleotide (Peebles et al., 1993). The ribozyme reaction described here, like the first step of the full splicing reaction, is inhibited by the presence of a +1 C, while any other nucleotide can function at that position. Although the reaction reported here is clearly distinct from SER, we consider SER to be a reaction related to the first step of group II intron splicing. If a group II intron does not rapidly release ligated exon products, they may be susceptible to another nucleophilic attack at the splice junction. A common misconception is that the SER reaction is a reversal of the second step of splicing. Strictly speaking, this is impossible given that the second step of group II intron splicing occurs exclusively (and quite rapidly) through a transesterification in which the leaving group is the 3'-hydroxyl of the lariat or linear intron (Jarrell et al., 1988(b)). Water is not the leaving group in the forward reaction, so water cannot be the attacking nucleophile in a reaction that is truly the reverse.

TABLE 2

Kinetic effects of base changes at the ribozyme cleavage site

| Substrate¥ | $k_{obs}$ (min–1)§ | relative rate |
|---|---|---|
| +1G (WT) | 0.036† | 1.0 |
| +1A | 0.053† | 1.5 |
| +1U | 0.028† | 0.79 |
| +1C | 0.0019‡ | 0.05 |
| ligated exons | 0.0068‡ | 0.19 |

Table 2 Legend:
¥ The sequence of transcribed substrates used to monitor mutational effect at the 5'-splice site is 5'-GGUGUGGUGGGACAUUUUC˘NAGCGGUU, (Seq. ID No. 10) where N marks the +1 nucleotide at the cleavage site. The sequence of the ligated exons substrate is 5'-GGAGUGGUGGGACAUUUUC˘ACUAUGUA, (Seq. ID No. 11) where the underlined nucleotides are 3'-exon sequences. Rates are not affected by identity of the first three 5'-nucleotides.
§ All rates were obtained simultaneously so it is exptectd that their relative error is very low (<5%). The absolute error for $k_{obs}$ values reported in this study is ±19% with 95% confidence (see legend, Table 1).
† Pseudo-first order plots were linear for at least four reaction half-times (as in FIG. 9) and empirically determined endpoints of 92–94% were used for data correction.
‡ For these slower substrates, <20% reaction extent, using a 92% endpoint was used in calculation of $k_{obs}$.

REFERENCES

1. Umesono, M. F. and Ozeki, H. (1989) *Gene* 82: 5–30
2. Kuck, U., et al. (1990) *U. Nucl. Acids Res.* 18: 2691–2697
3. Peebles, C. L., et al. (1986) *Cell* 44: 213–223
4. van der Veen, R., et al. (1986) *Cell* 44: 225–234
5. Jarrell, K. A., et al. (1988) *J. Biol. Chem.* 263: 3432–3439
6. Jarrell, K. A., et al. (1988) *Mol. Cell. Biol* 8: 2361–2366
7. van der Veen, R., et al. (1987) *EMBO* 6: 3827–3831
8. Jacquier, A. and Roshbash, M. (1986) *Science* 234: 1099–1104
9. Altura, R., et al. (1989) *M. Nucl. Acids Res.* 17: 335–354
10. Koch, J. L., et al. (1992) *Mol. Cell. Biol.* 12: 1950–1958
11. Franzen, J. S., et al. (1993) *Nucl. Acids Res.* 21: 627–634
12. Pyle, A. M. and Green, J. B. (1994) *Biochem.* 33: 2716–2725
13. Zaug, A. J. and Cech, T. R. (1986) *Science* 231: 470–475
14. Zaug, A. J., et al. (1986) *Science* 324: 429–433

15. Cech, T. R., et al. (1992) *J. Biol. Chem.* 267: 17479–17482
16. Jacquier, A. and Michel, F. (1987) *Cell* 50: 17–29
17. Jacquier, A. and Michel, F. (1990) *J. Mol. Biol.* 213: 437–447
18. Herschlag, D. and Cech, T. R. (1990) *Biochem.* 29: 10159–10171
19. Fedor, M. J. and Uhlenbeck, O. C. (1992) *Biochem.* 31: 12042–12054
20. Lamond, A. I. (1993) *Nature* 365: 294–295
21. Moore, M. J. and Sharp, P. A. (1993) *Nature* 365: 364–368
22. Moore, M. J., et al. (1993) *The RNA World* eds. Gesteland, R. and Atkins J., Cold Spring Harbor Laboratory Press, Cold Spring Harbor, pp303–357
23. Cavalier-Smith, T. (1991) *TIBS* 7: 145–148
24. Burgers, P. M. J. and Eckstein, F. (1979) *Biochemistry* 18: 592–596
25. Herschlag, D., et al. (1991) *Biochem.* 30: 4844–4854
26. Griffiths, A., et al. (1987) *Nucl. Acids Res.* 15: 4145–4162
27. Boguski, M. S., et al. (1979) *J. Biol. Chem* 255: 2160–2163
28. Donis-Keller, H., et al. (1977) *Nucl. Acids REs.* 4: 2527–2538
29. Potter, V. L., et al. (1983) *Biochem* 22: 1369–1376
30. Schatz, D., et al. (1991) *Proc. Natl. Acad Sci. USA* 88: 6132–6136
31. Peebles, C. L., et al. (1987) *Cold Spring Harbor Symp. Quant. Biol.* 52: 223–232
32. Chanfreau, G. and Jacquier, A. (1994) *EMBO J.*
33. Peebles, C. L., et al. (1993) *J. Biol. Chem* 268: 11929–11938
34. Suchy, M. and Schmelzer, C. (1991) *J. Mol. Biol.* 222: 179–187
35. Maschhoff, K. L. and Padgett, R. A. (1993) *Nucl. Acids Res.* 21: 5456–5462
36. Sharp, P. A. (1985) *Cell* 42: 397–400
37. Cech, T. R. (1986) *Cell* 44: 207–210
38. Bachl, J. and Schmelzer, C. (1990) *J. Mol. Biol.* 212: 113–125
39. Scaringe, S. A., et al. (1990) *Nucl. Acids Res.* 18: 5433–5441
40. Berget, S. M., et al. (1977) *Proc. Natl. Acad. Sci. USA* 74: 3171–3175
41. Chow, L. T., et al. (1977) *Cell* 12: 1–8
42. Brody, E. and J. Abelson (1985) *Science* 228: 963–967
43. Guthrie, C. (1991) *Science* 253: 157–163
44. Kruger, K., et al. (1982) *Cell* 31: 147–157
45. Cech, T. R. (1986) *Cell* 44: 207–210
46. Peebles, C. L., et al. (1986) *Cell* 44: 213–223
47. van der Veen, R., et al. (1986) *Cell* 44: 225–234
48. Jacquier, A. (1990) *TIBS* 15: 351–354
49. Michel, F., et al. (1989) *Gene* 82: 5–30
50. Bachl, J. and C. Schmelzer (1990) *J. Mol. Biol.* 212: 113–125
51. Kwakman, J. H. J. M., et al. (1989) *Nucl. Acids Res.* 17: 4205–4216
52. Jacquier, A. and N. Jacquesson-Breuleux (1991) *J. Mol. Biol.* 219: 415–428
53. Jarrell, K. A., et al. (1988) *Mol. Cell. Biol.* 8: 2361–2366
54. Pyle, A. M., et al. (1990) *Proc. Natl. Acad. Sci. USA* 87: 8187–8191
55. Pyle, A. M. and T. R. Cech (1991) *Nature* 350: 628–631
56. Pyle, A. M., et al. (1992) *Nature* 358: 123–128
57. Wissinger, B., et al. (1992) *Trends in Genetics* 8: 322–328
58. Perlman, P. S. and R. A. Butow (1989) *Science* 246: 1106–1109
59. Lambowitz, A. M. and P. S. Perlman (1990) *TIBS* 15: 440–444
60. Lambowitz, A. M. (1989) *Cell* 56: 323–326
61. Sharp, P. A. (1985) *Cell* 42: 397–400
62. Moore, M. J., et al. (1993) *The RNA World* 1–30
63. McSwiggen, J. A. and T. R. Cech (1989) *Science* 244: 679–683
64. Rajogopal, J., et al. (1989) *Science* 244: 692–694
65. Cech, T. R., et al. (1992) *J. Biol. Chem.* 267: 17479–17482
66. Jarrell, K. A., et al. (1988) *J. Biol. Chem.* 263: 3432–3439
67. Weeda, G., et al. (1990) *Cell* 62: 777–791
68. Sokai, E. and N. Tsuchida (1992) Oncogene 7: 927–933
69. Weerasinghe, M., et al. (1991) *J. Virology* 65: 5531–5534
70. Rossi, J. J., et al. (1991) *Pharmacology and Therapeutics* 50: 245–254
71. Guthrie, C. and B. Patterson (1988) *Ann. Rev. Gen.* 22: 387–419
72. Noller, H. F., et al. (1992) *Science* 256: 1416–1419
73. Jacquier, A. and M. Rosbash (1986) *Science* 234: 1099–1104
74. Fersht, A. (1985) *New York: W. H. Freeman* 98–118
75. Walstrum, S. A. and O. C. Uhlenbeck (1990) *Biochem.* 29: 10573–10576
76. Herschlag, D. and T. R. Cech (1990) *Biochem.* 29: 10159–10180
77. Zaug, A. J., et al. (1988) *Biochem.* 27: 8924–8931
78. Wyatt, J. R., et al. (1991) *Biotechniques* 11: 764–769
79. Kuck, U., et al. (1990) *Nucl. Acids Res.* 18: 2691–2697
80. Hebbar, S. K., et al. (1992) *Nucl. Acids Res.* 20: 1747–1754
81. Latham, J. A. and T. R. Cech (1989) *Science* 245: 276–282
82. Celander, D. W. and T. R. Cech (1991) *Science* 251: 401–407
83. Stubbe, J. and J. W. Kozarich (1987) *Chemical Reviews* 87: 1107–1136
84. Piccirilli, J. A., et al. (1993) *Nature* :in press
85. Green, R. and J. W. Szostak (1992) *Science* 258: 1910–1915
86. van der Horst, G., et al. (1991) *Proc. Natl. Acad. Sci. USA* 88: 184–188
87. Usman, N., et al. (1987) *J. Am. Chem. Soc.* 109: 7845–7854
88. Usman, N. and R. Cedergren (1992) *TIBS* 17: 334–339
89. Wu, T., et al. (1989) *Nucl. Acids Res.* 17: 3501–3517
90. Scaringe, S. A., et al. (1990) *Nucl. Acids Res.* 18: 5433–5441
91. Wang, J.-F., et al. (1992) *Manuscript submitted*
92. Smith, D., et al. (1992) *J. Biol. Chem.* 267: 2429–2436
93. Tuerk, C. and L. Gold (1990) *Science* 249: 505–510
94. Inouye, T. and T. R. Cech (1985) *Proc. Natl. Acad. Sci. USA* 82: 648–652
95. Quigley, G. J. and A. Rich (1976) *Science* 194: 796–806
96. Krol, A. and P. Carbon (1989) *Methods Enzymol* 180: 211–227
97. Ehresmann, C., et al. (1987) *Nucl. Acids Res.* 15: 9109–9128
98. Diaz, J.-J., et al. (1991) *BioTechniques* 11: 204–211
99. Chowrira, B.-M. and J. M. Burke (1991) *Biochem.* 87: 8518–8522
100. Fedor, M. J. and O. C. Uhlenbeck (1990) *Proc. Natl. Acad. Sci. USA* 87: 1668–1672

101. Freier, S. M., et al. (1986) *Proc. Natl. Acad. Sci. USA* 83: 9373–9377
102. Herschlag, D., et al. (1991) *Biochem* 30: 4844–4954
103. Herschlag, D. (1991) *Proc. Natl. Acad. Sci. USA* 88: 6921–6925
104. Herschlag, D. (1992) *Biochem* 31: 1386–1399
105. Young, B., et al. (1991) *Cell* 67: 1007–1019
106. Morl, M., et al. (1992) *Cell* 70: 803–810
107. Moore, M. J. and P. A. Sharp (1992) *Science* 256: 992–997
108. Seela, F. and T. Grein (1992) *Nucl. Acids Res.* 20: 2297–2306
109. Gott, J. M., et al. (1991) *Biochem* 30: 6290–6295
110. Tanner, N.-K., et al. (1988) *Biochem* 27: 8852–8861
111. Bevilacqua, P. C., et al. (1992) *Science* 258: 1355–1358
112. Wasserman, D. A. and J. A. Steitz (1992) *Science* 257: 1918–1925
113. Kunkel, T. A., et al. (1991) *Methods Enzymol* 204: 125–139

TABLE 1

Kinetic Parameters for Substrate Cleavage by the Group II Ribozyme:

| substrate | rate-limiting component[†] | $k_{max}$ (min$^{-1}$)[§] | $K_m$ (nM)[§] | $k_{max}/K_m$ (M$^{-1}$ min$^{-1}$)hu ¥ | $k_{obs}$ thioS (min$^{-1}$)[‡] | thio-effect** on $k_{max}$ |
|---|---|---|---|---|---|---|
| $S_{(synthetic)}$ | D1 | 0.021 ± 0.0010 | 6.3 ± 0.88 | (3.3 ± 0.49) × 10$^6$ | 0.012 | 1.8 |
| $S_{(synthetic)}$ | D1 | 0.032 ± 0.0048[††] | — | — | 0.0094 | 3.4 |
| $S_{(synthetic)}$ | D5 | 0.019 ± 0.0010 | 870 ± 110 | (2.2 ± 0.30) × 10$^4$ | — | — |

Figure 5A:
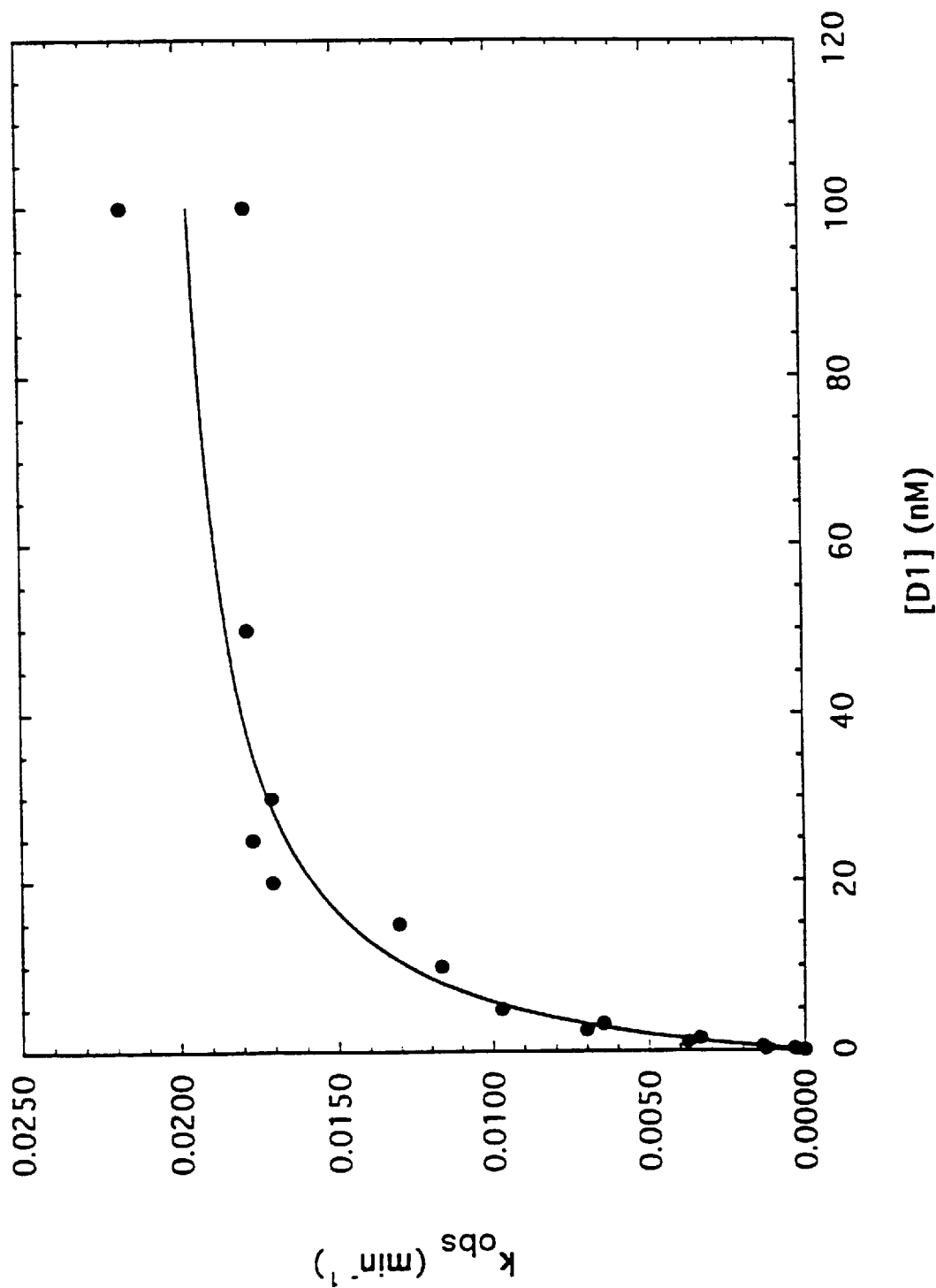
Figure 5B:
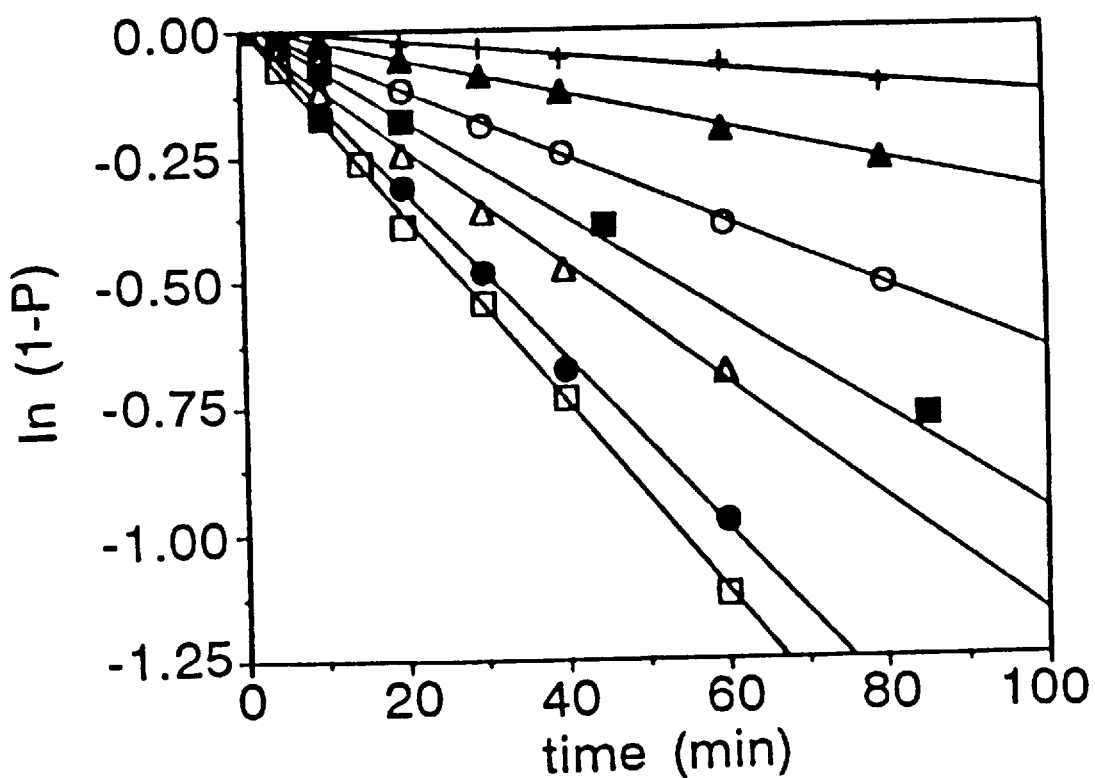

Table 1 legend:
[†]Described in legend to FIG. 5.
[§]$k_{max}$ represents the maximum rate at saturation and represents the horizontal asymptote derived from the binding curves shown in FIG. 5. Theoretical $k_{max}$ values at ∞D1 and ∞D5 were calculated from the data shown in FIG. 5 and found to be in agreement with a value of 0.026 min$^{-1}$ determined experimentally at 100 nM D1 and 9 μM D5. $K_m$ represents the apparent binding constant of the limiting component. These values were determined from the fit of the curves shown in FIG. 5 to an equation describing 1:1 bimolecular association[12]. The standard error for the fit is shown. The appropriateness of the standard error calculation was confirmed using a jackknife approximation of standard error[12].
¥$k_{max}/K_m$ (analogous to $k_{cat}/K_m$ values determined from the slopes of $k_{obs}$ vs. [D1] or [D5] at very low concentrations. Reported error was propagated from the $k_{max}$ and $K_m$ standard errors.
[‡]The reported rates represent $k_{obs}$ values for phosphorothioate substrates at saturation, where [D1] = 100 nM and [D5] = 3 μM (analogous to the plateau of the curve in FIG. 5A). Each value is the average of two trials. Like all reported $k_{obs}$, variance is 18% (see legend to FIG. 5A). The empirically determined endpoint (after 7 reaction half-times) used in calculation of $k_{obs}$ was 82% for the transcribed substrate and 48% for the synthetic substrate.
**The ratio of $k_{max}$ to $k_{obs}$ for phosphorothioate substrates at saturation.
[††]This value is the $k_{obs}$ at D1 and D5 saturation for cleavage of a transcribed all-phosphate substrate.

---

What is claimed is:

1. A synthetic non-naturally occurring nucleic acid molecule comprising:
   a) nucleotides hating a sequence which defines a conserved group II intron catalytic region;
   b) nucleotides having a sequence which hybridizes with a predetermined target sequence to be cleaved, and
   c) nucleotides having a sequence which defines a conserved portion of a group II intron domain V.

2. The molecule of claim 1, wherein the conserved group II intron catalytic region is a group II intron domain I catalytic region.

3. The molecule of claim 2, wherein the conserved group II intron domain I catalytic region further comprises a conserved portion of a group II intron domain II, a group II intron domain III, a group II intron domain IV, a group II intron domain V, or a group II intron domain VI.

4. The molecule of claim 1, wherein the sequence of part (b) is 2 to 12 nucleotides in length.

5. The molecule of claim 1, wherein the sequence of part (b) is 6 or 7 nucleotides in length.

6. The molecule of claim 1, wherein the molecule comprises from about 80 nucleotides to about 1000 nucleotides.

7. The molecule of claim 1, wherein the conserved portion of the group II intron domain V has the formula:

$$\begin{array}{ccc} 3' & (X)_n & (X)_{n'} & 5' \\ & X & * & X \\ & X & \ddagger & A \\ & X & \ddagger & G \\ & G & * & C \\ & (X)_c & * & (X)_{c'} \\ & G & \ddagger & U \end{array}$$

(with loop: $(X)_d$—X, $(X)_a$, $(X)_{d'}$, A—X)

(Seq. ID No. 3) wherein each X represents a ribonucleotide which may be the same or different; wherein each of $(X)_n$, $(X)_{n'}$, $(X)_c$, $(X)_{c'}$, $(X)_{d'}$, $(X)_a$ and $(X)_d$ represents an oligonucleotide; wherein n, n', c, c', d, d', and a each represents an integer which defines the number of nucleotides in the oligonucleotide with the provisos that n and n' are greater than or equal to 1; a represents an integer which is greater than or equal to 1; d and d' represent an integer which is greater than or equal to 5; c and c' represents an integer which is greater than or equal to 4; wherein each * represents base pairing between the nucleotide located on either side thereof; wherein each ‡ may or may not represent base pairing between the nucleotide located on either side thereof; and wherein each solid line represents a chemical linkage providing covalent bonds between the nucleotide located on either side thereof.

8. The molecule of claim 1, further comprising an associated divalent cation.

9. The molecule of claim 1, wherein the divalent cation is $Mg^{2+}$ or $Mn^{2+}$.

10. The molecule of claim 1, wherein the predetermined target sequence to be cleaved is DNA.

11. The molecule of claim 1, wherein the predetermined target sequence to be cleaved is mRNA.

12. The molecule of claim 11, wherein the mRNA encodes a growth factor.

13. The molecule of claim 12, wherein the growth factor is an angiogenic factor, a basic fibroblast growth factor, a colony-stimulating factor 1, cystic fibrosis transmembrane conductance regulator, an epidermal growth factor, an erythropoietin, a fibroblast growth factor, a G-protein, a granulocyte-macrophage colony stimulating factor, a growth hormone, IL-1, IL-LR, IL-2, IL-2R, IL-4, IL-6, an insulin-like growth factor, an insulin-like growth factor 1, an interferon, an interleukin, a keratinocyte growth factor, luteinizing hormone receptor, MDR1, a nerve growth factor, a platelet derived growth factor, a scatter factor, a transforming growth factor α, a transforming growth factor β, a transforming growth factor, or a tumor necrosis factor.

14. The molecule of claim 11, wherein the mRNA encodes an oncogene or a tumor suppressor gene.

15. The molecule of claim 14, wherein the oncogene or tumor suppressor gene is bcl-2, bcr-abl, bek, BPV, c-abl, c-fes, c-fms, c-fos, c-H-ras, c-kit, c-myb, c-myc, c-mos, c-sea, cerbB, DCC, erbA, erbB-2, ets, fig, FSFV gp55, Ha-ras, HIV tat, HTLV-1 tat, JCV early, jun, L-myc, lck, LPV early, met, N-myc, NF-1, N-ras, neu, p53, Py mTag, pim-1, ras, RB, rel, retinoblastoma-1, SV-40 Tag, TGF-α, TGF-β, trk, trkB, v-abl, v-H-ras, v-jun, or WT-1.

16. The molecule of claim 11, wherein the mRNA is an mRNA associated with a chromosomal translocation.

17. The molecule of claim 14, wherein the oncogene or tumor suppressor gene has one or more point mutations.

18. The molecule of claim 11, wherein the mRNA is an mRNA whose overproduction is associated with a disease or neoplastic condition.

19. The molecule of claim 11, wherein the mRNA is a mammalian mRNA.

20. The molecule of claim 11, wherein the mRNA is a yeast mRNA.

21. A synthetic non-naturally occurring nucleic acid molecule comprising:
   a) nucleotides having a sequence which defines a conserved group II intron catalytic region,
   b) two regions of nucleotides each having a sequence which hybridizes with a predetermined target sequence to be cleaved, and
   c) nucleotides having a sequence which defines a conserved portion of a group II intron domain V.

22. A composition comprising:
   a) a synthetic non-naturally occurring nucleic acid molecule comprising:
      i) nucleotides having a sequence which defines a conserved group II intron catalytic region, and
      ii) nucleotides having a sequence which hybridizes with a predetermined target sequence to be cleaved; and
   b) a separate nucleotide sequence which defines a conserved portion of a group II intron domain V.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

GGAGUGGUGG GACAUUUUCG AGCGGUU 27

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:2:

CGUGGUGGGA CAUUUCGAG CGGU 24

( 2 ) INFORMATION FOR SEQ ID NO:3:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:3:

```
GGAAUCGA                                                                                         8
```

( 2 ) INFORMATION FOR SEQ ID NO:4:

( i ) SEQUENCE CHARACTERISTICS:
        ( A ) LENGTH: 452 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:4:

```
GUGGUGGGAC  AUUUUCGAGC  GGUCUGAAAG  UUAUCAUAAA  UAAUAUUUAC  CAUAUAAUAA      60
UGGAUAAAUU  AUAUUUUUAU  CAAUAUAAGU  CUAAUUACAA  GUGUAUUAAA  AUGGUAACAU     120
AAAUACGCUA  AGCUGUAAUG  ACAAAAGUAU  CCAUAUUCUU  GACAGUUAUU  UUAUAUUAUA     180
AAAAAAAGAU  GAAGGAACUU  UGACUGAUCU  AAUAUGCUCA  ACGAAAGUGA  AUCAAAUGUU     240
AUAAAAUUAC  UUACACCACU  AAUUGAAAAC  CUGUCUGAUA  UUCAAUUAUU  AUUUAUUAUU     300
AUAUAAUUAU  AUAAUAAUAA  UAAAUAAAAU  GGUUGAUGUU  AUGUAUUGGA  AAUGAGCAUA     360
CGAUAAAUCA  UAUAACCAUU  AGUAAUAUAA  UUUGAGAGCU  AAGUUAGAUA  UUUACGUAUU     420
UAUGAUAAAA  CAGAAUAAAC  CCUAUAAAUU  AU                                    452
```

( 2 ) INFORMATION FOR SEQ ID NO:5:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:5:

```
UAUAUUUAGA  GGGUAAAAGA  UUGUAUAAAA  AGCUAAUGCC  AUAUUGUAAU  GAUACGGAUA     60
AGAAUUAUUA  UUCCAAAGAU  GAAAAUCUGC  UAACUUAUAC  UAUAGGUGAU  AUGCC         115
```

( 2 ) INFORMATION FOR SEQ ID NO:6:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:6:

```
AAGAUAUUGC  GUGAGCCGUA  UGCGAUGAAA  GUCGCACGUA  CGGUCUUAC   CGGGGAAAA     60
CUUGUAAAGG  UCUACCUAUC  GGGAUACUAU  G                                    91
```

( 2 ) INFORMATION FOR SEQ ID NO:7:

( i ) SEQUENCE CHARACTERISTICS:
    ( A ) LENGTH: 266 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:7:

| | | | | | | |
|---|---|---|---|---|---|---|
| GUCUUUAUGG | ACAGAUAACA | ACAUAUAUUA | UUCAUACAUU | AAAUAAUUAU | UUUAAUGAAU | 60 |
| GGAAUCUACG | CAUCUUAGUU | AAUUUGAUGA | CAUAAUAAUU | AUUAUUUUAU | UAAGUAAGAU | 120 |
| CGAUGUCUAA | UGACAUAAAC | AAUAUUUUUU | UCUAUUAUUA | AUUAAUAAAU | AAUAAUAAAU | 180 |
| AAAAAUAAUU | AUUGAAAGAA | GAUCAUCUGU | CUAAAUUAUC | GUUAAUUCAC | GUAAAUCGAU | 240 |
| GAAAAAUAAU | AUAUGGGAU | UUUCCA | | | | 266 |

( 2 ) INFORMATION FOR SEQ ID NO:8:

( i ) SEQUENCE CHARACTERISTICS:
        ( A ) LENGTH: 174 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:8:

| | | | | | | |
|---|---|---|---|---|---|---|
| UAUAGAAUCA | UGAAUUAUAU | AUAAUGAUCA | AAUUAUUUAU | AUAUUUUAAU | AAAAAUAUAU | 60 |
| UAAUAAUGGU | UAAUAUUAUU | AUUAAUUAAU | UAAUUAAUUA | AUUAAUAAUA | AUAACGAAUA | 120 |
| AAUGAUUGGC | ACAUAUAGAU | AUAUAGUAUA | UAUUUAUAUA | GGUUAACAUC | UCAC | 174 |

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

GGAGUGGUGG GACAUUUUCA GCGGUU                                                26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

GGUGUGGUGG GACAUUUUCA GCGGUU                                                26

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

(xi) SEQUENCE DESCRIPTION: SEQ ID NO:11:

GGAGUGGUGG GACAUUUUCA CUAUGUA    27